US009034390B2

(12) United States Patent
Kielbania, Jr.

(10) Patent No.: US 9,034,390 B2
(45) Date of Patent: May 19, 2015

(54) ANTI-MICROBIAL COMPOSITION AND METHOD FOR MAKING AND USING SAME

(75) Inventor: Andrew Kielbania, Jr., Chalfont, PA (US)

(73) Assignee: BIONEUTRAL LABORATORIES CORPORATION, Basking Ridge, NJ (US)

( * ) Notice: Subject to any disclaimer, the term of this patent is extended or adjusted under 35 U.S.C. 154(b) by 688 days.

(21) Appl. No.: 11/746,975

(22) Filed: May 10, 2007

(65) Prior Publication Data

US 2007/0258915 A1    Nov. 8, 2007

Related U.S. Application Data

(63) Continuation-in-part of application No. 11/381,269, filed on May 2, 2006, now abandoned.

(51) Int. Cl.
| | |
|---|---|
| A61K 33/40 | (2006.01) |
| A61K 47/00 | (2006.01) |
| A61K 47/30 | (2006.01) |
| A61K 31/19 | (2006.01) |
| A01N 37/00 | (2006.01) |
| A61L 9/14 | (2006.01) |
| A01N 59/00 | (2006.01) |
| A61L 2/18 | (2006.01) |
| A61L 2/22 | (2006.01) |

(52) U.S. Cl.
CPC ............... *A61L 9/145* (2013.01); *A01N 59/00* (2013.01); *A61L 2/186* (2013.01); *A61L 2/22* (2013.01); *A61L 2202/17* (2013.01)

(58) Field of Classification Search
None
See application file for complete search history.

(56) References Cited

U.S. PATENT DOCUMENTS

| | | | |
|---|---|---|---|
| 3,912,451 A | 10/1975 | Gaglia, Jr. | |
| 3,982,892 A | 9/1976 | Gray | |
| 4,051,058 A | 9/1977 | Bowing et al. | |
| 4,051,059 A | 9/1977 | Bowing et al. | |
| 4,404,191 A | 9/1983 | Sporkenbach et al. | |
| 4,431,631 A | 2/1984 | Clipper et al. | |
| 4,536,314 A | 8/1985 | Hardy et al. | |
| 4,537,778 A | 8/1985 | Clipper et al. | |
| 4,743,447 A | 5/1988 | Le Rouzic et al. | |
| 5,116,575 A | 5/1992 | Badertscher et al. | |
| 5,171,564 A | 12/1992 | Nathoo et al. | |
| 5,296,239 A | 3/1994 | Colery et al. | |
| 5,344,652 A * | 9/1994 | Hall et al. ................. 424/405 |
| 5,436,008 A * | 7/1995 | Richter et al. ............ 424/405 |
| 5,489,706 A | 2/1996 | Revell | |
| 5,508,646 A | 4/1996 | Cortiula | |
| 5,589,106 A | 12/1996 | Shim et al. | |
| 5,605,687 A | 2/1997 | Lee | |
| 5,616,616 A | 4/1997 | Hall, II et al. | |
| 5,656,302 A | 8/1997 | Cosentino et al. | |
| 5,840,343 A | 11/1998 | Hall, II et al. | |
| 5,900,256 A | 5/1999 | Scoville, Jr. et al. | |
| 6,197,784 B1 | 3/2001 | Fuchs et al. | |
| 6,290,935 B1 | 9/2001 | Masters et al. | |
| 6,346,279 B1 | 2/2002 | Rochon | |
| 6,348,187 B1 | 2/2002 | Pan et al. | |
| 6,585,933 B1 | 7/2003 | Ehrhardt et al. | |
| 6,656,426 B1 | 12/2003 | Wang et al. | |
| 6,683,040 B2 | 1/2004 | Bragulla et al. | |
| 6,686,325 B2 | 2/2004 | Hoyt et al. | |
| 6,693,069 B2 | 2/2004 | Korber et al. | |
| 6,696,093 B2 | 2/2004 | Ney et al. | |
| 6,716,457 B1 | 4/2004 | Eagles et al. | |
| 6,720,355 B2 | 4/2004 | Prusiner et al. | |
| 6,767,569 B1 | 7/2004 | Marsden et al. | |
| 6,790,380 B2 * | 9/2004 | Sato et al. ................. 252/186.23 |
| 6,797,681 B2 | 9/2004 | Fricker et al. | |
| 6,828,294 B2 | 12/2004 | Kellar et al. | |
| 6,908,891 B2 | 6/2005 | Biering et al. | |
| 6,936,434 B2 | 8/2005 | McDonnell et al. | |
| 6,953,507 B2 * | 10/2005 | Kravitz et al. ............ 134/26 |
| 6,998,369 B2 | 2/2006 | Hei et al. | |
| 7,001,873 B2 | 2/2006 | McDonnell et al. | |
| 7,008,592 B2 | 3/2006 | Sias et al. | |
| 7,049,277 B2 | 5/2006 | Bragulla et al. | |
| 7,074,374 B1 | 7/2006 | Fujii et al. | |
| 7,129,080 B2 | 10/2006 | Antloga et al. | |
| 2006/0233886 A1 | 10/2006 | Kielbania, Jr. et al. | |
| 2006/0293202 A1 | 12/2006 | Cate et al. | |

FOREIGN PATENT DOCUMENTS

WO    WO 96/13247    *    5/1996

OTHER PUBLICATIONS

Disenfection, Sterilization, and Preservation, by Seymour Stanton Block, published by Lippincott Williams & Wilkins, 2000.*
Soap Definition Webster's New World College Dictionary, 4th Ed. http://www.yourdictionary.com/soap.*

* cited by examiner

*Primary Examiner* — Tigabu Kassa
(74) *Attorney, Agent, or Firm* — Antonio Papageorgiou, Esq.; Meister Seelig & Fein LLP

(57) ABSTRACT

The present invention generally relates to anti-microbial formulations and methods of their use and production. The formulations of the present invention are effective as broad spectrum anti-bacterial agents with efficacy against both Gram-negative and Gram-positive bacteria, as anti-viral agents with efficacy against both enveloped and non-enveloped viruses, and as anti-fungal agents with efficacy against both vegetative and spore forms of microorganisms and against biofilms. The present invention includes anti-microbial compositions that have at least one surfactant, at least one acid, at least one peroxide (preferably hydrogen peroxide), peracetic acid, and water. The anti-microbial Formulations of the present invention may additionally contain an organic salt. The organic salt may be a salt of the same acid that is used in the Formulation or a salt of a different acid. Methods for production and use of the inventive compositions are disclosed.

20 Claims, No Drawings

ANTI-MICROBIAL COMPOSITION AND METHOD FOR MAKING AND USING SAME

CROSS-REFERENCE TO RELATED APPLICATION

This application is a continuation-in-part application of parent application Ser. No. 11/381,269, filed May 2, 2006, now abandoned the entire contents of which are incorporated herein by reference.

BACKGROUND OF THE INVENTION

1. Field of the Invention

The present invention relates to chemical formulation that possess anti-bacterial, antiviral, anti-fungal, sterility, and spermicidal properties which are not corrosive to ferrous metals and methods of making and using those formulations.

2. Description of the Related Art

Microorganisms, e.g., bacteria, viruses, and fungi (e.g., mold, both in the vegetative and spore form) are a major source of disease and contamination throughout modern society. The need to control the growth of these micro-organisms is paramount for maintaining public health as well as reducing costly commercial and industrial contamination. In the case of bacteria, infections and contaminations are effected by both Gram-positive (e.g., *Staphylococcus aurous*) and Gram-negative (e.g., *Escherichia coli*) bacteria. Many anti-bacterial agents are limited in their efficacy to only one of those two classes of bacteria. Moreover, known anti-viral agents are often effective only against enveloped or non-enveloped viruses, but not both. As used herein, the terms anti-microbial agents and anti-microbial compositions mean, without limitation, anti-bacterial, anti-viral, anti-fungal, sterility, spermicidal, biocide, disinfectant, sanitizing, antiseptic, and/or mildewicidal agents and compositions.

While numerous anti-microbial agents exist, many have the further limitation that they cannot be compounded into formulations for extended transport over concerns regarding degradation of stability and/or efficacy. Thus, there has been a long standing need for stable and efficacious anti-microbial formulations that possess broad spectrum activity. In addition there is a long standing need for anti-microbial formulations that do not detract, diminish or destroy the integrity of surfaces and substrates that the anti-microbial agent makes contact with. Therefore four features: broad spectrum effectiveness, rapid speed to kill, stability, and noncorrosivness, especially to ferrous metals, are highly desired features of anti-microbial agents. However, up to now these features have been unattainable without the use of auxiliary agents which complicate the anti-microbial formulation and often are antagonistic to one another, leading to inactive anti-microbial agents or anti-microbial agents of limited stability.

In order to achieve highly efficacious and broad spectrum anti-microbial agents, peroxy compounds are often part of the formulation. These peroxy compounds include hydrogen peroxide, alkyl peroxides, peresters, percarbonates, persulfates and peracids. U.S. Pat. No. 6,998,369 of Hei et al., the entirety of which is incorporated herein by reference, provide an extensive review of effective anti-microbial agents.

While peroxy compounds are effective at eradicating harmful microorganisms, they are corrosive to metals, especially ferrous metals. This is a significant drawback since many surfaces, articles, and instruments such as surgical and dental equipment, endoscopes, catheters, and surgical rooms are made of or have components containing ferrous metals such as iron, steel and various grades of stainless steel. Corrosion of ferrous metals by anti-microbial agents is therefore unacceptable. To attempt to overcome the apparent inherent corrosive property of peroxy compounds in anti-microbial formulations, various types of corrosion inhibitors are also incorporated into the anti-microbial formulation. U.S. Pat. No. 6,585,933, of Ehrhardt et al., the entirety of which is incorporated herein by reference provide an extensive description of various corrosion inhibiting approaches. However, the inclusion of additional components, such as, corrosion inhibitors, to anti-microbial formulations can be disadvantageous and detrimentally effect the anti-microbial efficacy of the composition. These other components can result in loss of clarity causing nonhomogeneous formulations, compromise efficacy by interfering with the anti-microbial agent's activity, or reduce stability and shorten the useable lifetime of an anti-microbial formulation.

SUMMARY OF THE INVENTION

I have discovered formulations which have the desired features of broad spectrum anti microbial effectiveness, rapid speed of kill, stability, and noncorrosivness, especially to ferrous metals. The present invention generally relates to anti-microbial formulations and methods of their use and production. The formulations of the present invention are effective as broad spectrum anti-bacterial agents with efficacy against both Gram-negative and Gram-positive bacteria, as anti-viral agents with efficacy against both enveloped and non-enveloped viruses, and as anti-fungal agents with efficacy against both vegetative and spore forms of microorganisms and against biofilms.

As used herein, an anti-bacterial or bactericide means a substance that kills bacteria.

As used herein, an antiseptic means an anti-microbial substance that is applied to living tissue or skin to reduce the possibility of infection, sepsis, or putrefaction.

As used herein, an anti-viral or viricide is a substance that "kills" viruses outside the body, i.e., an antiseptic which reliably deactivates or destroys a virus.

As used herein, an anti-fungal or fungicide is a substance that kills, and/or prevent the spread of fungi.

As used herein, a sporicide is a substance that destroys spores.

As used herein, a mildewicide is a substance that kills mildew.

As used herein, a biocide is a substance capable of killing different forms of living organisms. Biocides may be used in fields such as medicine, agriculture, forestry, and mosquito control. Biocides include, but are not limited to, (1) pesticides, which include fungicides, herbicides, insecticides, algaecides, moluscicides, miticides, and rofenticides, and/or (2) antimicrobials, which include germicides, antibiotics, anti-bacterials, anti-virals, anti-fungals, anti-protozoals, anti-parasites, and spermicides.

As used herein, a sterilant is an anti-microbial substance that is capable of eliminating all forms of microbial life, including spores.

As used herein, a disinfectant is an anti-microbial substance that is applied to non-living objects to destroy microorganisms, the process of which is known as disinfection.

As used herein, a sanitizer or sanitizing agent is an anti-microbial substance that may be applied to both living and non-living objects and which kills over 99.9% of a target microorganism in applicable situations.

As used herein, the term "anti-microbial effective amount" means an amount of the inventive composition which is sufficient to kill or retard the growth of a substantial number of microbes to which the inventive composition is applied so as to achieve the desired level of ineffectiveness of the microbes.

As used herein, all amounts expressed in percent by weight are based on percent by weight of the total weight of the composition.

The present invention includes anti-microbial compositions that have at least one surfactant, at least one acid, at least one peroxide (preferably hydrogen peroxide), peracetic acid, and water. The anti-microbial Formulations of the present invention may additionally contain an organic salt. The organic salt may be a salt of the same acid that is used in the Formulation or a salt of a different acid. More particularly, I have discovered an anti-microbial composition comprising:

at least one surfactant present in a concentration from about 0.02 to about 50% by weight;

at least one acid or acid salt present in a concentration of up to about 20% by weight;

at least one peroxide present in a concentration of up to about 20% by weight.

at least one peracid present in a concentration of up to about 30% by weight.

the balance water, wherein the amount of anti-microbial agent is effective to produce a Zone of Inhibition of from 25 to 70 mm and for the composition to exhibit Plate Cidality against each of *Staphylococcus aureus* ATCC 6538, *Escherichia coli* ATCC 8739, *Pseudomonas aeruginosa* ATCC 9027 and *Candida albicans* ATCC 10231 at aqueous dilutions up to 1:2000 and is CPE positive.

An important feature of one embodiment of the present invention is related to the use of three individually corrosive components of an anti-microbial formulation which when combined correctly, in accordance with the invention into an anti-microbial formulation provides a non-corrosive formulation, especially one which is non-corrosive to ferrous metals, that has broad spectrum anti microbial effectiveness, rapid speed to kill and stability.

In a first embodiment, I have discovered that the inventive efficacious, rapid acting, stable, and non-corrosive anti-microbial formulations can be prepared by combining a surfactant, an acid or acid salt, a peroxide and a peracid wherein a specific ratio of acid to peroxide to peracid is present in the formulation to provide a broad spectrum, rapid acting, stable, and non-corrosive, especially to ferrous metals, anti-microbial formulation. A procedure is described herein for preparing the inventive formulation.

In yet another embodiment, I have discovered that the inventive efficacious, rapid acting, stable and non-corrosive anti-microbial formulations can be prepared when a surfactant, an acid or acid salt, and a peroxide are first heated above room temperature for about 30 minutes and then cooled to room temperature. A peracid is then combined into the formulation. A minimum ratio of acid to peroxide to peracid is present in the formulation to provide a broad spectrum, rapid acting, stable, and non-corrosive anti-microbial formulation. A procedure for forming this formulation is also described herein.

DETAILED DESCRIPTION OF THE INVENTION

The present invention broadly relates to broad spectrum, rapid speed to kill, stable, and in one embodiment, non-corrosive, especially to ferrous metals, anti-microbial compositions comprising at least one surfactant, at least one acid, at least one peroxide, at least one peracid, optionally water, and optionally a low molecular weight alcohol. As used herein, "low molecular weight alcohol" means an alkyl alcohol wherein the alkyl group contains from one to eight carbon atoms. Specific examples include butyl alcohol, propyl alcohol, ethyl alcohol, methyl alcohol and butyl cellusolve. The anti-microbial formulations of the present invention may additionally contain an organic salt. The organic salt may be a salt of the same acid that is used in the formulation or a salt of a different acid.

The anti-microbial formulations of the present invention include a surfactant. The surfactant used in the present formulations may be anionic or nonionic. The preferred anionic surfactants are members of the following classes of chemical compounds: alkyl sulfates, alkylethoxylated sulfates, alkyl aromatic sulfonates, alkyl sulfosuccinates, dialkyl sulfosuccinates, alkylethoxylated sulfosuccinates, dialkylethoxylated sulfosuccinates. Specific examples include: sofium lauryl sulfate, sofium laurylethoxy sulfate, sofium dofecylbenzene sulfonate, disofium 2-ethylhexyl sulfosuccinate, sofium lauryl sulfosuccinate, sofium laurylethoxy sulfosuccinate.

The preferred nonionic surfactants are members of the following classes of chemical compounds: alkyl ethoxylates, alkylaryl ethoxylates, ethylene oxide/propylene oxide diblock and triblock surfactants both linear and branched. Specific examples include: secondary alcohol ethoxylate (Tergitol™ 15-S-40), lauryl ethoxlate(12), octylphenol ethoxylate 7.5 (Triton™ X-114), nonylphenol ethoxylates, alkyl ethoxylates (Plurafac® Surfactants).

Particularly preferred surfactants that may be used in the present invention include Pluronic® Polyols, Pluronic® R Polyols, Pluronic® F-38 Polyols, Pluronic® F-88, Polyols, Tetronic® Polyols, Tetronic® R Polyols available from BASF Corporation. These preferred block copolymer surfactants, both linear and branched, vary in molecular weight from about 1,000 to 27,000, have a propylene oxide block portion of molecular weight from about 800 to 5,000 and vary in ethylene oxide content from about 10% to 80%. They can be in liquid, paste or solid form depending upon the molecular weight and amount of propylene oxide and ethylene oxide contained in the block copolymer surfactant. Specific examples include: Pluronic® L31, L43, L61, L121, F87, F108, F127; Pluronic® R 10R8, 17R8, 25R5, 31R4; Tetronic® 304, 901, 1102, 1304, 1502; Tetronic® R 50R8, 70R4, 90R8, 150R7.

The ability to have a large family of block nonionic ethylene oxide/propylene oxide surfactants provides considerable flexibility in selecting nonionic surfactants with specific characteristics (e.g., water or solvent solubility, solvent characteristics to dissolve a variety of organic compounds, wetting, foaming, detergency, etc.). These characteristics can systematically be tabulated in what BASF Corporation refers to as the "Pluronic Grid", and simplifies the selection of a surfactant (1) for a specific application or (2) that has specific attributes or characteristics. These nonionic ethylene oxide/propylene oxide surfactants are often referred to as "poloxamers". Nonionic surfactants, particularly, ethlylene oxide/propylene oxide diblock and triblock type poloxamers, are attractive in formulations that contain highly reactive or unstable components, such as peroxide and peracids, since these surfactants contain no charges that will react with other compounds. In addition, ethlylene oxide/propylene oxide diblock and triblock type poloxamers surfactants, in particular, can readily solvate or stabilize reactive components, since unlike traditional surfactants they have no critical micelle concentration value but instead aggregate. These aggregation and nonreactive properties of ethlylene oxide/propylene oxide diblock and triblock type poloxamer surfactants makes these surfactants unlike other traditional nonionic surfactants, such as, alkyl ethoxylates and alkyl aryl ethoxylates. Poloxamer surfactants therefore have properties different from the traditional nonionic surfactants. For example, the aggregation and nonreactive characteristics of poloxamers renders poloxamers mild to the skin and eyes, and also can mitigate irritation since traditional surfactants are more irritating or are outright irritants.

A single surfactant of the types listed above may be used in the anti-microbial formulations. Alternatively, anti-microbial formulations that include multiple surfactants are also considered as within the scope of this present invention. The examples of surfactants listed above are not an exhaustive list of the surfactants that may be used in the present invention. One skilled in the art will recognize additional members and variations within the various categories listed above. Such additional compounds are considered to be within the scope of the present invention.

The anti-microbial agents that are preferably employed in the present invention are non-cationic anti-microbial agents. The non-cationic anti-microbial agents may be phenolics, halogenated phenolics, halogenated diphenyl ethers, halogenated carbonilides, water soluble or water insoluble peroxy oxidizing agents, for example, peroxides, peresters, peracids, percarbonates, persulfates or mixtures thereof. The incorporation of solid anti-microbial agents into the present invention provides long lasting efficacy for the anti-microbial formulation of the present invention.

More specifically, typical anti-microbials include:
Phenolics:
  Phenol
  Xylenol
  2-nitrophenol
  2-phenyl phenol-
Halogenated phenolics:
  2,3-dichlorophenol
  2,4-dichlorophenol
Halogenated diphenyl ethers
  Triclosan
Peroxides: diacyl peroxides; dialkyl peroxides; diperoxyketals; hydroperoxides; ketone peroxides; peroxyesters
  Dicumyl peroxide
  Lauroyl peroxide
  Decanoyl peroxide
  Benzoyl peroxide
  Succinic acid peroxide
  2,5-di(t-butyl peroxy)-2,5-dimethyl hexane
  t-butyl cumyl peroxide
  bis(t-butylperoxy)diisopropylbenzene
  di(t-amyl)peroxide
  di(t-butyl)peroxide
  2,5-di(t-butylperoxy)-2,5-dimethyl-3 hexyne
  1,1di(t-butyl peroxy)-3,3,5-trimethylcyclohexane
  1,1di(t-butylperoxy)cyclohexane
  1,1di(t-amylperoxy)cyclohexane
  n-butyl-4,4-di(t-butylperoxy)valerate
  ethyl-3,3-di(t-amylperoxy)butanoate
  ethyl-3,3-di(t-butylperoxy)butyrate
  cumene hydroperoxide
  t-butyl hydroperoxide
  methyl ethyl ketone peroxide
  2,4-pentanedione peroxide
  and hydrogen peroxide
  3-hyroxy-1,1-dimethyl butyl peroxyneofecanoate
  alpha-cumyl peroxyneofecanoate
  t-amyl peroxyneofecanoate
  t-amyl peroxypivalate
  t-butyl peroxypivalate
  2,5-di(2-ethylhexanoylperoxy)-2,5-dimethylhexane
  t-amyl peroxy-2-ethylhexanoate
  t-butyl peroxy-2-ethylhexanoate
  t-amyl peracetate
  t-butyl peracetate
  t-butyl perbenzoate
  t-butyl peroxy-3,5,5-tri methyl hexanoate
Peracids:
  Peracetic acid
  Peroxymonosulfuric acid
  Perchloric acid
  Perpropronic acid
  Perbenzoic acid
  m-chloroperbenzoic acid
Persulfates:
  Sofium persulfate
  Ammonium persulfate
Percarbonates and Perborates:
  di(npropyl)peroxydicarbonate
  di(sec-butyl)peroxydicarbonate
  di(2-ethyl hexyl)peroxydicarbonate
  Sofium carbonate peroxide
  OO(t-amyl)-O-(2-ethyl hexyl)monoperoxycarbonate
  OO(t-amyl)-O-isopropylmonoperoxycarbonate
  OO(t-butyl)-O-(2-ethylhexyl)monoperoxycarbonate
  poly-t-butylperoxy carbonate
  Sofium perborate.

The anti-microbial formulations of the present invention include an acid or acid salt. Various carboxylic acids can be used. Preferably, the acids are dicarboxylic acids or tricarboxylic acids or tetracarboxylic acids or higher such as polycarboxylic acids, such as (co)polyacrylic acid, (co)polymethacrylic acid, (co)polymaleic acid and anhydride. Preferred acids include, oxalic, malonic, succinic, glutaric, adipic, pimelic, suberic, azelaic, sebacic, maleic, fumaric, itaconic, phthalic, terphthalic, isophthalic, ethylenediaminetetraacetic, trimellitic, hemimellitic, salicylic, and citric. Citric acid and phthalic acid are the preferred acids and trisofium citrate and mono or di sofium or potassium phthalate are the preferred salts. These acids can be used individually or as mixtures of two or more including in combination with monocarboxlyic acids such as acetic, proprionic, lactic, formic, salicylic, or benzoic acids. In addition the lithium, sofium, potassium, and ammonium salts of these acids—monosalts or multiple cation salts—can be used in the present invention. The use of acid salts can increase the solubility of acids of low water solubility and can be used to change or raise the pH of formulations of the present invention. The examples of acids and acid salts listed above are not an exhaustive list of the acids that may be used in the present invention. One skilled in the art will recognize additional members and variations within the various categories listed above. Such additional compounds are considered to be within the scope of the present invention.

The formulations of the present invention may also include a wetting agent at a concentration of up to about 3%, by weight. For example, commercially available wetting agents, such as, fluorocarbon and silicone based wetting agents are particularly effective.

The formulations of the present invention may also include other additives, such as fragrance, colors, inorganic salts, inorganic acids, sequesterants, organic solvents, fillers, rheology modifiers, and thickeners. The formulations of the present invention containing the various components indicated hereinabove may be in the form of a liquid, viscous liquid, liquid (e.g., a liquid soap), a pasty mixture (e.g., a heavy-duty soap used by mechanics), or a semi-solid or solid (e.g., a bar of soap). This form depends on the solids content of the formulation, and the present invention contemplates all of such forms. However, the form of the inventive composition does not affect its anti-microbial properties. The anti-microbial formulations of the present invention can be used as prepared, or diluted to about 1 to 1000 with water, water solutions, alcohols, or alcohol solutions. Alcohols having from one to eight carbon atoms can be used. Methanol, ethanol, 1-propanol, 2-propanol, 1-butanol, 2-butanol, butyl cellusolve, neopentyl alcohol and t-butanol are the preferred alcohols. Optionally, peroxide stabilizers, such as colloidal stannate, sodium pyrophosph and organophosphonates can be included in the inventive composition. The inventive formulation, in such forms, may have components in the following amounts.

| | Range | Preferred Range | Most Preferred Range |
|---|---|---|---|
| Surfactant | 0.02-98% | 0.05-50% | 0.1-15% |
| Acid or Acid Salt | 0.1-20% | 0.4-15% | 0.6-10% |
| Peroxide | 0.1-20% | 0.4-15% | 0.7-10% |
| Peracid | 0.05-30% | 0.2-20% | 0.3-14% |
| Alcohol | 0-30% | 0-20% | 0-10% |
| Remainder Water | | | |

In this present invention I have found that the specific ratio of formulation components determines both the efficacy and, more surprisingly, the lack of corrosiveness towards ferrous metals of the composition. Using the specific examples of citric acid, and hydrogen peroxide, and peracetic acid as the peroxy components, the following ratios of component weight percentages for the active ingredient provide anti-microbial formulations with broad spectrum efficacy, rapid time to kill, stability, and non-corrosiveness to ferrous metals:

| Component | Ratio of Citric Acid to - | Ratio of Hydrogen Peroxide to | Ratio of Peracetic Acid to |
|---|---|---|---|
| Ratio Range | 0.2-6 | 0.2-6 | 0.6-2.5 |
| Preferred Ratio Range | 0.6-5 | 0.6-5 | 0.8-1.7 |
| Most Preferred Ratio Range | 0.7-3 | 0.7-3 | 1-1.4 |

The above ratios are not corrected for any hydrogen peroxide that may be present in the solution of peracetic acid. The following list of anti-microbial formulations of the present invention exemplifies the most preferred compositions within the most preferred weight ratio ranges of active citric acid to hydrogen peroxide to peracetic acid:

| weight % of Pluronic ™ Surfactant and Type | weight % Citric Acid | weight % Hydrogen Peroxide | weight % Peracetic Acid | weight % t-butyl hydroperoxide |
|---|---|---|---|---|
| 6% L-31 | 3 | 3 | 3 | — |
| 6% L-43 | 3 | 3 | 3 | — |
| 4% L-31 | 3 | 3 | 3 | — |
| 4% L-43 | 3 | 3 | 3 | — |
| 6% L-43 | 2 | 1.9 | 3 | — |
| 6% L-43 | 3 | 3 | 3 | 3 |
| 6% L-31 | 2 | 1.5 | 2 | — |
| 6% L-31 | 2 | 2.6 | 2 | — |
| 6% L-31 | 2 | 3.9 | 2 | — |
| 6% L-31 | 1 | 1.9 | 2 | — |
| 6% L-31 | 1.5 | 1.9 | 2 | — |
| 6% L-31 | 2.5 | 1.9 | 2 | |
| 6% L-31 | 4 | 1.9 | 2 | |
| 6.0% L-43 | 1.2 | 1.2 | 0.3 | |
| 0.6% L-43 | 1.2 | 1.2 | 0.3 | 3.0 |

The above examples demonstrate the preferred weight percentage ratio of active citric acid to hydrogen peroxide to peracetic acid. When other acids, acid salts, peroxides, or peracids are used, the preferred ratios can be determined by considering the components' equivalent weights. For example, if t-butyl hydroperoxide is used to replace the hydrogen peroxide, about 2.6 times more t-butyl hydroperoxide would be equivalent to the amount of hydrogen peroxide since that is the difference of the two component's equivalent weights, which translates into a corresponding change in the preferred weight percentage ratios of formulation components. The same correction can be made when other acids, acid salts, or peracids are utilized in the present invention. In the following tables the percentage of components is expressed as weight percent of active ingredient on total formulation weight.

The following list of anti-microbial formulations with peroxy anti-microbial agents are examples of formulations which are not stable and continuously degas for at least 3 days which is a sign of the degradation of the peroxy component(s) of the formulation.

| weight % of Surfactant and Type | weight % Citric Acid | weight % Hydrogen Peroxide | weight % Peracetic Acid | weight % t-butyl hydroperoxide |
|---|---|---|---|---|
| 4.3% cocobetaine | — | 2.3 | 2.6 | — |
| 3.9% cocobetaine | — | 2.1 | 2.5 | 5.9 |
| 4.6% cocamidopropylbetaine | — | 2.3 | 2.6 | — |
| 3.0% cocobetaine | 1.4 | 9.9 | 2.0 | — |
| 3.0% cocobetaine | 1.4 | 17.8 | 2.0 | — |
| 4.6% cocamidopropylbetaine | 0.8 | 2.3 | 2.0 | — |
| 4.6% octylbetaine | — | 2.3 | 2.0 | — |
| 4.6% laurylbetaine | — | 2.3 | 2.0 | — |
| 4.6% caprylamidopropylbetaine | — | 2.3 | 2.0 | — |
| 4.6% cocamidopropylhydroxysultaine | — | 2.3 | 2.0 | — |
| 4.6% laurylhydroxysultaine | — | 2.3 | 2.0 | — |

The above list demonstrates that with a variety of functional surfactants, peroxy anti-microbial formulations have limited stability.

Table 1 demonstrates that if all three components—acid, peroxide, and peracid—are not present a peracid antimicrobial formulation that is corrosive to ferrous metals will result.

color of the solution (sol) along with the extent of corrosion or rusting (rust) of the nail are noted. A comment of "rust" indicates that the nail was completely covered with oxidized material. A comment of "total rust" indicates that the nail is totally covered with oxidized material to such an extent that the shape of the nail is distorted—extremely severe corrosion.

TABLE 1

| Example Number | % weight Surfactant and Type | % weight Citric Acid | % weight Hydrogen Peroxide | % weight Peracetic Acid | Corrosion after 2 Hours | Corrosion after 19 Hours | Corrosion after 2 weeks |
|---|---|---|---|---|---|---|---|
| 1 | 6% Pluronic ® L-31 | 2.0 | 0 | 2.0 | Brown sol and rust | Tan-brown sol and rust | Yellow sol and total rust |
| 2 | 8.3% Pluronic ® F-108 | 0 | 2.5 | 2.9 | Red-brown sol and rust | Red-brown sol and rust | Red-brown sol and total rust |
| 3 | 6% Pluronic ® L-43 | 2.0 | 0 | 2.0 | Tan sol and rust | Tan sol and rust | Yellow sol and total rust |
| 4 | 6% Pluronic ® L-43 | 0 | 1.9 | 2.0 | Red-brown sol and rust | Red-brown sol and rust | Red-brown sol and total rust |
| 5 | 6% Pluronic ® L-43 | 0 | 0 | 2.0 | Orange-red sol and rust | Orange-red sol and total rust | Orange-red sol and total rust |
| 6 | 6% Pluronic ® L-31 | 0 | 1.9 | 2.0 | Red-brown sol and rust | Red-brown sol and total rust | Red-brown sol and total rust |
| 7 | 6% Pluronic ® L-31 | 0 | 0 | 2.0 | Red-brown sol and rust | Red-brown sol and total rust | Red-brown sol and total rust |
| 8 | 6% Pluronic ® F-87 | 0 | 0 | 2.0 | Orange-red sol and rust | Orange-red sol and total rust | Orange-red sol and total rust |
| 9 | 6% Pluronic ® F-87 | 2.0 | 0 | 2.0 | Orange sol and rust | Orange sol and total rust | Yellow sol and total rust |
| 10 | 6% Pluronic ® F-87 | 0 | 1.9 | 2.0 | Red sol and rust | Red sol and total rust | Brown sol and total rust |

The corrosion test conducted in Table 1 was performed as follows at room temperature: a 4D bright finishing nail, 1.5 inches in length distributed by Primesource Building Products and available at Lowe's Building Centers (any similar uncoated and not rust inhibited common nail can be used), is placed in a 10 ounce crystal clear plastic glass, manufactured by Waddington North America Inc. and available at Costco. To the glass with the nail are added about 15 milliliters of the anti-microbial formulation to be tested. The 15 ml completely covers the nail. All anti-microbial formulations of the present invention are initially clear and colorless—unless a water insoluble surfactant is used which results in a hazy mixture or emulsion—and are also stable since no degassing or pressure build up is observed in the bottles used for storage. The various formulations tested ranged in pH from about 1 to about 7. The glass and contents are covered with a clear plastic food wrap to prevent the liquid formulation from evaporating. No agitation of the samples are required, this is a static test. The contents of the glass are visually inspected at the time intervals indicated in the tables. Both the clarity and A comment of "clear, no rust" indicates that the anti-microbial formulation is not corrosive to ferrous metals. This corrosion test involving a common bright finishing nail is particularly difficult to pass because of the ease at which uncoated, unprotected, unalloyed to resist corrosion iron will corrode in the presence of oxidizing agents. Formulations that are corrosive usually show signs of corrosion in 2 hours or less and this degree of corrosiveness is unacceptable for anti-microbial formulations since articles made of ferrous metals are very common and would rather quickly be rendered useless. To be a viable anti-microbial formulation, it should not cause any corrosion on common iron in less than a 2 week period at room temperature. The other tables that follow use the same corrosion test protocol. The results in Table 1 indicate that if either citric acid or hydrogen peroxide or both are absent from the formulation, severe corrosion of ferrous metals will occur.

Table 2 demonstrates that when all three components—acid, peroxide and peracid—are present but not at the required ratio, a formulation corrosive to ferrous metals will result.

TABLE 2

| Example Number | % weight Surfactant and Type | % weight Citric Acid | % weight Hydrogen Peroxide | % weight Peracetic Acid | Ratio Citric Acid to Hydrogen Peroxide to Peracetic acid | Corrosion after 2 Hours | Corrosion after 19 Hours | Corrosion after 2 weeks |
|---|---|---|---|---|---|---|---|---|
| 11 | 6% Pluronic ® L-31 | 2.0 | 0.5 | 2.0 | 1:.25:1 | Brown sol and rust | Brown sol and total rust | Brown sol and total rust |
| 12 | 6% Pluronic ® L-31 | 2.0 | 1.0 | 2.0 | 1:0.5:1 | Brown sol and rust | Brown sol and total rust | Brown sol and total rust |
| 13 | 6% Pluronic ® L-31 | 0.5 | 1.9 | 2.0 | 0.25:0.95:1 | Brown sol and rust | Brown sol and total rust | Brown sol and total rust |
| 14 | 6% Pluronic ® L-31 | 2.0 | 1.9 | 4.0 | 0.5:0.48:1 | Light Yellow sol | Brown sol and total rust | Brown sol and total rust |
| 15 | 6% Pluronic ® L-31 | 2.0 | 1.9 | 6.0 | 0.33:0.32:1 | Light Yellow sol | Light Yellow sol | Brown sol and total rust |
| 16 | 6% Pluronic ® L-31 | 2.0 | 1.9 | 8.0 | 0.25:0.24:1 | Light Yellow hazy sol | Light Yellow hazy sol | Light Yellow hazy sol localized pitting |
| 17 | 3% Pluronic ® L-31 | 2.0 | 1.9 | 4.0 | 0.5:0.48:1 | Light Brown sol and rust | Brown sol and total rust | Brown sol and total rust |
| 18 | 3% Pluronic ® L-31 | 2.0 | 1.9 | 8.0 | 0.25:0.24:1 | Brown sol and rust | Brown sol and total rust | Brown sol and total rust |
| 19 | 3% Pluronic ® L-43 | 2.0 | 1.9 | 8.0 | 0.25:0.24:1 | Light Yellow sol | Brown sol and total rust | Dark Brown sol and total rust |
| 20 | 6% Pluronic ® L-31 | 2.0 | 1.9 | 3.0 | 0.67:0.63:1 | Light Yellow sol | Light Brown sol and total rust | Brown sol and total rust |
| 21 | 6% Pluronic ® L-43 | 2.0 | 1.9 | 3.0 | 0.67:0.63:1 | Light Yellow sol | Light Brown sol and total rust | Brown sol and total rust |
| 22 | 4% Pluronic ® F-108 | 2.0 | 0.50 | 2.0 | 1:.25:1 | Brown sol | Brown sol and total rust | Brown sol and total rust |

The results in Table 2 indicate the presence of only citric acid and hydrogen peroxide is insufficient to prevent corrosion of ferrous metals. These components must be present in the correct ratio to provide formulations that do not corrofe ferrous metals.

Table 3 demonstrates that individual aqueous solutions of citric acid, hydrogen peroxide, or peracetic acid are corrosive to ferrous metals.

TABLE 3

| Example Number | % weight Surfactant and Type | % weight Citric Acid | % weight Hydrogen Peroxide | % weight Peracetic Acid | Ratio Citric Acid to Hydrogen Peroxide to Peracetic acid | Corrosion after 2 Hours | Corrosion after 19 Hours | Corrosion after 2 weeks |
|---|---|---|---|---|---|---|---|---|
| 23 | None, only water | 0 | 0 | 2.1 | 0:0:2.1 | Dark Brown sol and total rust | Dark Brown sol and total rust | Dark Brown sol and total rust |
| 24 | None, only water | 0 | 15 | 0 | 0:15:0 | Bubbles and grayish discoloration | The nail accelerates the decomposition of the hydrogen peroxide | |
| 25 | None, only water | 2.0 | 0 | 0 | 2:0:0 | Hazy sol and rust | Hazy sol and rust | Hazy sol and rust |

Table 4 demonstrates that when all three components, i.e., the acid, peroxide, and the peracid, are present at the required ratio, an anti-microbial, formulation which is non-corrosive to ferrous metals will be obtained.

TABLE 4

| Example Number | % weight Surfactant and Type | % weight Citric Acid | % weight Hydrogen Peroxide | % weight Peracetic Acid | Ratio Citric Acid to Hydrogen Peroxide to Peracetic acid | Corrosion after 2 Hours | Corrosion after 19 Hours | Corrosion after 2 weeks |
|---|---|---|---|---|---|---|---|---|
| 26 | 2% each Pluronic ® L-31, F-127, L-121 | 2.0 | 2.6 | 2.0 | 1:1.3:1 | Clear, no rust | Clear, no rust | Clear, no rust |
| 27 | 3% each Pluronic ® L-31, L-121 | 2.0 | 1.9 | 2.0 | 1:0.95:1 | Slight haze, no rust | Slight haze, no rust | Slight haze, no rust |
| 28 | 2% Pluronic ® L-31 | 2.0 | 1.9 | 2.0 | 1:0.95:1 | Clear, no rust | Clear, no rust | Clear, no rust |
| 29 | 6% Pluronic ® F-87 | 2.0 | 1.9 | 2.0 | 1:0.95:1 | Clear, no rust | Clear, no rust | Clear, no rust |
| 30 | 6% Pluronic ® L-43 | 2.0 | 1.9 | 2.0 | 1:0.95:1 | Clear, no rust | Clear, no rust | Clear, no rust |
| 31 | 3% each Pluronic ® L-31, L-43 | 2.0 | 1.9 | 2.0 | 1:0.95:1 | Clear, no rust | Clear, no rust | Clear, no rust |
| 32 | 3% each Pluronic ®- L-31, L-61 | 2.0 | 1.9 | 2.0 | 1:0.95:1 | Clear, no rust | Clear, no rust | Clear, no rust |
| 33 | 6% Pluronic ®- L-31 | 2.0 | 1.5 | 2.0 | 1:0.75:1 | Clear, no rust | Clear, no rust | Clear, no rust |
| 34 | 6% Pluronic ® L-31 | 2.0 | 2.6 | 2.0 | 1:0.1.3:1 | Clear, no rust | Clear, no rust | Clear, no rust |
| 35 | 6% Pluronic ® L-31 | 2.0 | 3.9 | 2.0 | 1:0.1.95:1 | Clear, no rust | Clear, no rust | Clear, no rust |
| 36 | 6% Pluronic ® L-31 | 1.0 | 1.5 | 2.0 | 0.5:0.75:1 | Clear, no rust | Clear, no rust | Clear, no rust |
| 37 | 6% Pluronic ® L-31 | 1.5 | 1.5 | 2.0 | 0.75:0.75:1 | Clear, no rust | Clear, no rust | Clear, no rust |
| 38 | 6% Pluronic ® L-31 | 2.5 | 1.5 | 2.0 | 1.25:0.75:1 | Clear, no rust | Clear, no rust | Clear, no rust |
| 39 | 6% Pluronic ® L-31 | 4.0 | 1.5 | 2.0 | 2:0.75:1 | Clear, no rust | Clear, no rust | Clear, no rust |
| 40 | 4% Pluronic ® L-31 | 2.0 | 1.9 | 2.0 | 1:0.95:1 | Clear, no rust | Clear, no rust | Clear, no rust |
| 41 | 2% Pluronic ® L-31 | 2.0 | 1.9 | 2.0 | 1:0.95:1 | Clear, no rust | Clear, no rust | Clear, no rust |
| 42 | 1% Pluronic ® L-31 | 2.0 | 1.9 | 2.0 | 1:0.95:1 | Clear, no rust | Clear, no rust | Clear, no rust |
| 43 | 10% Pluronic ® L-31 | 2.0 | 1.9 | 2.0 | 1:0.95:1 | Clear, no rust | Clear, no rust | Clear, no rust |
| 44 | 6% Pluronic ® L-43 | 2.0 | 1.9 | 8.0 | 0.25:0.24:1 | Clear, no rust | Clear, no rust | Clear, no rust |
| 45 | 3% Pluronic ® L-31 | 2.0 | 1.9 | 2.0 | 1:0.95:1 | Clear, no rust | Clear, no rust | Clear, no rust |
| 46 | 3% Pluronic ® L-43 | 2.0 | 1.9 | 2.0 | 1:0.95:1 | Clear, no rust | Clear, no rust | Clear, no rust |
| 47 | 6% Pluronic ® L-31 | 3.0 | 3.0 | 3.0 | 1:1:1 | Clear, no rust | Clear, no rust | Clear, no rust |

TABLE 4-continued

| Example Number | % weight Surfactant and Type | % weight Citric Acid | % weight Hydrogen Peroxide | % weight Peracetic Acid | Ratio Citric Acid to Hydrogen Peroxide to Peracetic acid | Corrosion after 2 Hours | Corrosion after 19 Hours | Corrosion after 2 weeks |
|---|---|---|---|---|---|---|---|---|
| 48 | 6% Pluronic ® L-43 | 3.0 | 3.0 | 3.0 | 1:1:1 | Clear, no rust | Clear, no rust | Clear, no rust |
| 49 | 4% Pluronic ® L-31 | 2.0 | 1.9 | 3.0 | 0.67:0.63:1 | Clear, no rust | Clear, no rust | Clear, no rust |
| 50 | 4% Pluronic ® L-31 | 3.0 | 3.0 | 3.0 | 1:1:1 | Clear, no rust | Clear, no rust | Clear, no rust |
| 51 | 4% Pluronic ® L-43 | 2.0 | 1.9 | 3.0 | 0.67:0.63:1 | Clear, no rust | Clear, no rust | Clear, no rust |
| 52 | 4% Pluronic ® L-43 | 3.0 | 3.0 | 3.0 | 1:1:1 | Clear, no rust | Clear, no rust | Clear, no rust |
| 53 | 6% Pluronic ® L-31 | 4.0 | 4.0 | 4.0 | 1:1:1 | Clear, no rust | Clear, no rust | Clear, no rust |
| 54 | 6% Pluronic ® L-43 | 3.0 | 3.0 plus 2.9% t-butyl-hydroperoxide (TBHP) | 3.0 | 1:1.97:1 | Clear, no rust | Clear, no rust | Clear, no rust |
| 55 | 6% Triton ™ X-114 | 3.0 | 3.0 | 3.0 | 1:1:1 | Clear, no rust | Clear, no rust | Clear, no rust |
| 56 | 3% Pluronic ® L-43 | 2.0 | 1.9 | 1.5 | 1.3:1.3:1 | Clear, no rust | Clear, no rust | Clear, no rust |
| 57 | 3% Pluronic ® L-43 | 2.0 | 1.9 | 0.75 | 2.6:2.5:1 | Clear, no rust | Clear, no rust | Clear, no rust |

The anti-microbial formulations of the present invention are also non-corrosive to aluminum. The corrosion test was modified by replacing the steel nail with approximately one square inch of Reynolds Wrap® Quality Aluminum Foil. The formulation of example 26 showed no corrosion of the aluminum foil after two weeks at room temperature.

It appears also that Pluronic® L-43 provides a slight enhancement to the non-corrosiveness of the formulation compared to Pluronic® L-31.

We have also discovered that heating the acid and peroxide accelerates or increases the level of the desired associated material, along while removing any possible impeding materials. Table 5 demonstrates that by initially heating these components in a formulation that had a borderline acceptable ratio of components, and which initially was corrosive to ferrous metals, the formulation can be made non-corrosive to ferrous metals. The results in Table 5 should be compared with Examples 20 and 21 in Table 2.

TABLE 5

| Example Number | % weight Surfactant and Type | % weight Citric Acid | % weight Hydrogen Peroxide | % weight Peracetic Acid | Ratio Citric Acid to Hydrogen Peroxide to Peracetic acid | Corrosion after 2 Hours | Corrosion after 19 Hours | Corrosion after 2 weeks |
|---|---|---|---|---|---|---|---|---|
| 58 | 6% Pluronic ® L-31 | 2.0 | 1.9 | 3.0 | 0.67:0.63:1 | Clear, no rust | Clear, no rust | Clear, no rust |
| 59 | 6% Pluronic ® L-43 | 2.0 | 1.9 | 3.0 | 0.67:0.63:1 | Clear, no rust | Clear, no rust | Clear, no rust |

The results in Table 5 indicate that preheating the formulation before the addition of the peracid improves the non-corrosiveness to ferrous metals property of the anti-microbial formulation of the present invention compared to non-heated formulations.

Table 6 demonstrates that acids, or salts of acids, other than citric acid are also effective and can be used in the present invention.

TABLE 6

| Example Number | weight % Surfactant and Type | weight % Acid or acid salt | weight % Hydrogen Peroxide | weight % Peracetic Acid | Ratio Acid or salt to Hydrogen Peroxide to Peracetic acid | Corrosion after 2 Hours | Corrosion after 19 Hours | Corrosion after 2 weeks |
|---|---|---|---|---|---|---|---|---|
| 60 | 6% Pluronic ® L-31 | 2.0 monosodium phthalate | 1.9 | 2.0 | 1:0.95:1 | Clear, no rust | Clear, no rust | Clear, no rust |
| 61 | 6% Pluronic ® L-31 | 2.0 trisofium citrate | 1.9 | 2.0 | 1:0.95:1 | Clear, no rust | Clear, no rust | Clear, no rust |
| 62 | 6% Pluronic ® L-31 | 2.0 salicylic acid monosofium salt | 1.9 | 2.0 | 1:0.95:1 | Hazy sol, no rust | Brown sol, no rust | Brown sol, no rust |
| 63 | 6% Pluronic ® L-31 | 2.0 sofium benzoate | 1.9 | 2.0 | 1:0.95:1 | Clear, no rust | Clear, no rust | Clear, no rust |

The results in Table 6 indicate that acid salts other than citric acid salts can be used to prepare formulations that are not corrosive to ferrous metals.

Table 7 demonstrates that when all three components, the acid, peroxide, and peracid are present in the required ratio, a formulation which is noncorrosive to ferrous metals is obtained. Instead of a plain nail, a stainless steel washer was used to further exemplify the non-corrosive nature of the inventive anti-microbial formulations. The stainless steel washer is a 5/16 split lock washer manufactured by the Hillman Fastener Company of Cincinnati, Ohio. It is not a high grade of stainless steel that would be used in, for example, surgical instruments or endoscopes. Therefore this is also is a demanding test.

The results in Table 7 indicate that the anti-microbial formulations of the present invention are not corrosive to stainless steel.

Table 8 illustrates the stability of the anti-microbial formulation of the present invention. High density polyethylene bottles 60 ml in size are approximately half filled with the anti-microbial formulation of the present invention. After 19 hours and 1 week of storage at room temperature, the bottles were slowly opened and monitored to detect the sound of any escaping gas. No escaping gas could be detected in any of the samples of Table 8 indicating that these anti-microbial formulation of the present invention are stable.

TABLE 8

| Example Number | Pressure Build Up after 19 Hours | Pressure Build Up After One Week |
|---|---|---|
| 26 | No | No |
| 28 | No | No |
| 34 | No | No |
| 44 | No | No |

TABLE 7

| Example Number | % weight Surfactant and Type | % weight Citric Acid | % weight Hydrogen Peroxide | % weight Peracetic Acid | Ratio Citric Acid to Hydrogen Peroxide to Peracetic acid | Corrosion after 2 Hours | Corrosion after 19 Hours | Corrosion after 2 weeks |
|---|---|---|---|---|---|---|---|---|
| 26 | 2% each Pluronic ® L-31, F-127, L-121 | 2.0 | 2.6 | 2.0 | 1:1.3:1 | Clear, no rust | Clear, no rust | Clear, no rust |
| 51 | 4% Pluronic ® L-43 | 2.0 | 1.9 | 3.0 | 0.67:0.63:1 | Clear, no rust | Clear, no rust | Clear, no rust |
| 53 | 6% Pluronic ® L-31 | 4.0 | 4.0 | 4.0 | 1:1:1 | Clear, no rust | Clear, no rust | Clear, no rust |
| 55 | 6% Triton ™ X-114 | 3.0 | 3.0 | 3.0 | 1:1:1 | Clear, no rust | Clear, no rust | Clear, no rust |

TABLE 8-continued

| Example Number | Pressure Build Up after 19 Hours | Pressure Build Up After One Week |
|---|---|---|
| 47 | No | No |
| 48 | No | No |
| 50 | No | No |
| 52 | No | No |
| 53 | No | No |
| 57 | No | No |
| 60 | No | No |
| 61 | No | No |

Antimicrobial Efficacy Testing

Determination of Zone of Inhibition

Disks impregnated with known concentrations of anti-microbial compositions are placed onto the surface of Mueller-Hinton Agar 150 mm plates that have been freshly seeded with a known quantity of bacteria (varying from $10^5$ to $10^8$ cfus/ml). Numerous different bacteria can be challenged in this manner in order to determine the spectrum of activity of the agent. The standard inoculum is a 0.5 Mc Farland standard turbidity, which is approximately $1.5 \times 10^8$ cfu/ml. The surface of the agar is swabbed in three directions to ensure an even and complete distribution of inoculum over the entire plate. Within 15 minutes of inoculation, the anti-microbial agent are applied to the disks and the plates are inverted for incubation to avoid accumulation of moisture on the agar surface that might interfere with the interpretation of the test results. For most organisms, incubation is at 35° C. in air. Increased $CO_2$ is used with certain fastidious bacteria. The dynamics and timing of anti-microbial agent diffusion to establish a concentration gradient, coupled with the growth of organisms over an 18- to 24-hour duration, is critical for reliable results. Therefore incubation of disks beyond that allotted time should be avoided.

Using a dark background and a reflected light, the plate is situated so that a ruler or caliper may be used to measure the diameter of the zone of inhibition for each anti-microbial agent.

Zones are recorded in millimeters (mm) of diameter. Known controls (including media controls) are employed with each run to assure accuracy of the techniques employed. This Zone of Inhibition test was conducted using the formulations in the examples.

Plate Cidality

In order to determine whether the anti-microbial agent being tested exhibited Plate Cidality vs. no Plate Cidality, a loop full of inoculum was taken within the Zone of Inhibition approximately 2 mm from the disk edge after the plates have been incubated for 18-24 hours. The loop was inoculated to a fresh Trypticase Soy Agar plate and then incubated at 35° C. for 18-24 hours before being read. The results Are recorded as "No growth", indicating Plate Cidality or "Growth" indicating no Plate Cidality. Alternatively the number of colonies was recorded in cases where there was incomplete Plate Cidality.

Testing for Yeast and Mold Fungi

Disks impregnated with known concentrations of anti-microbials are placed onto the surface of Sabouraud Dextrose Agar 150 mm plates that have been freshly seeded with a known quantity of fungi. Numerous different yeast and mold fungi can be challenged in this manner in order to determine the spectrum of activity of the agent. The standard inoculum is a 0.5 Mc Farland standard turbidity, which is approximately $1.5 \times 10^8$ cfu/ml. This concentration is used for yeast fungi. For mold fungi, spores are harvested in PBS and using a hemocytometer, an approximate count is made guaranteeing an inocula of at least $1.5 \times 10^4$ to $10^5$ cfu/ml. The surface of the agar is swabbed in three directions to ensure an even and complete distribution of inoculum over the entire plate. Within 15 minutes of inoculation, the anti-microbial agent disk disks are applied, and the plates are inverted for incubation to avoid accumulation of moisture on the agar surface that might interfere with the interpretation of the test results. For most organisms, incubation is at 30-35° C. in ambient air dependent upon the fungal species. The dynamics and timing of anti-microbial agent diffusion to establish a concentration gradient coupled with the growth of organisms over a 24-48 hours duration for yeast fungi and up to 10 days for mold fungi is critical for reliable results.

Using a dark background and a reflected light, the plate is situated so that a ruler or caliper may be used to measure the diameters of the inhibition zone for each anti-microbial agent.

The diameters of the Zones are recorded in millimeters (mm). Known controls (including media controls) are employed with each run to assure accuracy of techniques employed.

Plate Cidality for Fungi

In order to determine whether the anti-microbial agent being tested had Plate Cidality vs. static or no Plate cidality, a loopful of inoculum was taken within the Zone of Inhibition approximately 2-4 mm from the disk edge after the plates have been incubated for the designated time. The loop is inoculated to a Sabauroud Dextrose Agar plate and then incubated at 30-35° C., for the appropriate time, depending upon whether it is a mold or yeast fungus, before reading the plate. The results are recorded as "No growth", indicating Plate Cidality, or "Growth", indicating no Plate Cidality. Alternatively the number of colonies are to be recorded in cases where there was incomplete Plate Cidality.

Shell Vial Culture for Viral Analysis

MRC-5 human embryonic diploid lung fibroblast cells are inoculated with a previously germicide treated ATCC culture of Herpes Simplex virus maintained in Eagle's minimum essential medium. The treatment is with a germicide to be tested at a 1:3 dilution held at room temperature for 1 hour prior to cell inoculation. Two shell vials are inoculated in this manner and then incubated at 35° C., one for 24 hours and the other for 48 hours. After incubation they are observed for cytopathic effect (CPE) using standard immunofluorescent staining. CPE negative is considered to be an effective kill of HSV. CPE positive is considered to be a failure. Positive and negative controls are run with all experiments.

Time to Kill Studies

The anti-microbial formulations are tested in a time to kill study with about an 8% spore population bacteria. Approximately 1.0 ml of the anti-microbial formulations are used in the study into which $10^8$ cfu/ml Are added and viable counts Are measured over time intervals. The time intervals are 1, 5, 15, and 30 minutes, and 1, 2, 4, 6, 8, 12, 24 and hours. Time intervals might be slightly different for different runs but and are indicated in the appropriate tables. At the designated time intervals about 1/1000 of an ml of solution was subcultured onto Petri dishes containing TSA (trypticase soy agar) with 5% Sheep Bloof. The plates are incubated for about 24 hours and the number of colonies are counted if the counts are less than 300, otherwise counts are recorded as TNTC (too numerous to count). The results are recorded as follows:

Time Remaining Colonies
1 min
5 min
10 min 30 min 1 hour 2 hours 3 hours 4 hours 6 hours 12 hours 24 hours Blank control Heavy growth, too numerous to count (TNTC)

Table 9 demonstrates the broad spectrum efficacy against representatives of both Gram positive and Gram negative microorganisms.

TABLE 9

| Antimicrobial Formulation Example # | Zone of Inhibition for S. aureus (mm) | Zone of Inhibition for E. coli (mm) | Plate Cidality for S. aureus | Plate Cidality for E. coli |
|---|---|---|---|---|
| 2 | 62 | 50 | Yes | Yes |
| 26 | 60 | 55 | Yes | Yes |
| 27 | 59 | 51 | Yes | Yes |
| 28 | 57 | 51 | Yes | Yes |
| 47 | 47 | 43 | Yes | Yes |
| 48 | 50 | 40 | Yes | Yes |
| 50 | 61 | 40 | Yes | Yes |
| 52 | 49 | 43 | Yes | Yes |
| 54 | 61 | 70 | Yes | Yes |
| 59 | 52 | 42 | Yes | Yes |
| 61 | 49 | 40 | Yes | Yes |
| 71 | 47 | 34 | Yes | Yes |
| 72 | 47 | 32 | Yes | Yes |
| 73 | 47 | 32 | Yes | Yes |
| 74 | 47 | 33 | Yes | Yes |
| 75 | 48 | 33 | Yes | Yes |
| 76 | 47 | 34 | Yes | Yes |
| 78 | 46 | 30 | Yes | Yes |
| 79 | 50 | 37 | Yes | Yes |
| 80 | 65 | 100 | Yes | Yes |
| 81 | 79 | 110 | Yes | Yes |
| 82 | 106 | 130 | Yes | Yes |
| 83 | 84 | 130 | Yes | Yes |
| 84 | 64 | 52 | Yes | Yes |
| 85 | 65 | 52 | Yes | Yes |

Table 10 demonstrates that the anti-microbial formulations, examples 47 and 48, of the present invention rapidly and completely eliminate the most hearty spore forms of microorganisms. In this table the spore form of Bacillus anthracis at a 15% concentration level is shown to be totally eliminated with exceptional speed. With *Bacillus anthracis* being an example of a remarkably hearty and difficult to kill spore form of a heath threatening microorganism the anti-microbial formulations of the present invention are capable of eradicating other difficult to kill microorganisms both in the vegetative and spore form, such as *Bacillus subtilus, clostridium difficile*, methicillin resistant *Staphylococcus aureus*, vancomycin-resistant Enterococci, multi-drug resistant *Pseudomonas aeruginosa*, Pan-resistant *Klebsiella pneumoniae, Escherichia coli*—AmC+, ESBL *Klebsiella pneumoniae, Klebsiella pneumoniae* McAMPC, Penicillin resistant *Staphylococcus pneumoniae, Acinetobacter baumi-nii, Candida albicans, Candida lusitaniae, Aspergillus fumigatus, Aspergillus niger, Candida glabrata*, in addition to the gram positive and gram negative microorganisms already shown in previous examples.

TABLE 10

Time to Kill *Bacillus anthracis* - 15% spore concentration level

| Time | Remaining Colonies with Example 47 | Remaining Colonies with Example 48 |
|---|---|---|
| 1 minute | TNTC | TNTC |
| 5 minutes | 0 | 0 |
| 10 minutes | 0 | 0 |
| 30 minutes | 0 | 0 |
| 1 hour | 0 | 0 |
| 2 hours | 0 | 0 |
| 3 hours | 0 | 0 |
| 4 hours | 0 | 0 |
| 6 hours | 0 | 0 |
| 12 hours | 0 | 0 |
| 24 hours | 0 | 0 |
| control | TNTC | TNTC |

Table 11 demonstrates that the anti-microbial formulations of the present invention can be made at high concentration, and Table 12 demonstrates that these concentrated formulations can then be diluted to a desired level or formulation.

TABLE 11

| Example # | % weight Surfactant and Type | % weight Citric Acid | % weight Hydrogen Peroxide | % weight Peracetic Acid |
|---|---|---|---|---|
| 64 | 6.0% Pluronic ® L-43 | 16.0 | 16.0 | 3.0 |
| 65 | 6.0% Pluronic ® L-43 | 14.0 | 14.0 | 3.0 |
| 66 | 6.0% Pluronic ® L-43 | 12.0 | 12.0 | 3.0 |
| 67 | 6.0% Pluronic ® F-108 | 12.0 | 12.0 | 3.0 |
| 68 | 6.0% Pluronic ® L-43 | 10.0 | 10.0 | 3.0 |

Table 12 demonstrates that the above concentrated formulations, contained in Table 11, can be diluted to a desired level of concentration. The concentrated antimicrobial formulations above can typically be diluted with water from 1 to 3 to 1 to 10 or even higher at 1 to 100. Also other components can be added to modify the diluted formulation. The anti-microbial formulations in Table 12 with 0.3% peracetic acid are non-corrosive to ferrous metals and give results similar to those observed in Tables 4, 5, and 6 using the previously described uncoated nail corrosion test.

TABLE 12

| Example # | % weight Surfactant and Type | % weight Citric Acid | % weight Hydrogen Peroxide | % weight Peracetic Acid |
|---|---|---|---|---|
| 69 | 0.6% Pluronic ® L-43 | 1.6 | 1.6 | 0.3 |
| 70 | 4.6% Pluronic ® L-43 | 1.6 | 1.6 | 0.3 |
| 71 | 0.6% Pluronic ® L-43 | 1.4 | 1.4 | 0.3 |
| 72 | 4.6% Pluronic ® L-43 | 1.4 | 1.4 | 0.3 |
| 73 | 0.6% Pluronic ® L-43 | 1.2 | 1.2 | 0.3 |
| 74 | 4.6% Pluronic ® L-43 | 1.2 | 1.2 | 0.3 |
| 75 | 0.6% Pluronic ® F-108 | 1.2 | 1.2 | 0.3 |
| 76 | 4.6% Pluronic ® F-108 | 1.2 | 1.2 | 0.3 |

TABLE 12-continued

| Example # | % weight Surfactant and Type | % weight Citric Acid | % weight Hydrogen Peroxide | % weight Peracetic Acid |
|---|---|---|---|---|
| 77 | 0.6% Pluronic ® L-43 | 1.0 | 1.0 | 0.3 |
| 78 | 4.6% Pluronic ® L-43 | 1.0 | 1.0 | 0.3 |
| 79 - this example was prepared using the same procedure as those formulations contained in Tables 1-4 and 6, 7 and not from concentrate | 6.0% Pluronic ® L-43 | 3.0 | 3.0 | 0.3 |

Uses of the Anti-Microbial Formulations of the Present Invention

The anti-microbial formulations of the present invention have broad spectrum effectiveness, rapid speed to kill, stability, and noncorrosivness especially to ferrous metals. They can be used to eradicate harmful microorganisms in a variety of applications. The anti-microbial formulations of the present invention can be applied in any context—to an object (both living and non-living, as well as fluid and solid), on a surface of an object, or into an enclosed space—as a liquid, a froth, a foam, a spray, a mist or a fog. An object, as used herein, means any visible or tangible item and may be indoors and outdoors. The anti-microbial formulations of the present invention can be used as cleaners, washes, disinfectants, sanitizers, antiseptics, sterilants, bactericides, sporicides, fungicides, virucides, mildewcides, or biocides where vegetative or spore forms of harmful or infectious microorganisms need to be reduced or eliminated by applying onto inanimate surfaces or surfaces that are alive. The concentrated antimicrobial compositions above can typically be diluted with water from 1 to 3 to 1 to 10 or even higher at 1 to 100.

Living objects include, but are not limited to, animals (e.g., humans, dogs, cats, horses, etc.) and plants (e.g., grass, trees, fruits, vegetables, etc.) With a human, the anti-microbial formulations of the present invention can be applied onto skin, nails, fingers, toes, teeth, gums, throat, tongue or hair. Prior to surgery the anti-microbial formulations of the present invention can be applied to the skin to prevent surgical site infections. These formulations can also be applied to accelerate the healing of wounds, cuts, abrasions and burns. In the oral care arena the anti-microbial formulations of the present invention can be used as a mouthwash and to maintain healthy gums, teeth, prevent mouth sores or mitigate the severity of mouth sores and sore throats. These formulations can also be used to brighten or whiten teeth. The anti-microbial formulation of the present invention can also be used as an additive for products used in the above applications to reduce or eliminate harmful microorganisms or prevent the new growth of harmful microorganisms.

With other animals, the anti-microbial formulations of the present invention can be applied on fur, hooves, hide, or skin. The anti-microbial formulations of the present invention can also be used in animal husbandry, animal care, and confined animal feeding areas. With non-living objects in the health care field, the anti-microbial formulations of the present invention can be applied to surfaces in the surgical theater, on surgical equipment, on diagnostic equipment, on catheters, and on endoscopes. These formulations can also be used in hospital rooms, bathrooms, and hallways, where textiles, woof, stone, concrete, ceramics, tiles, metals, hard and flexible plastics, and elastomeric surfaces and objects need to be treated to reduce or eliminate harmful or infectious microorganisms.

With objects in the food and beverage area, the anti-microbial formulations of the present invention can be used in the areas where processing, preparing, packaging, and storage operations occur. The anti-microbial formulation of the present invention can be used also to treat relevant objects in this field, including liquids, beverages, and water, that have been contaminated with harmful microorganisms, so as to render these objects safe for use. The anti-microbial formulation of the present invention can be also be used also to decontaminate, purify, or preserve these objects.

In addition to living and non-living objects, the anti-microbial formulations of the present invention can be applied to enclosed spaces, such as rooms, storage areas, living areas, recreation areas, closets, and air condition and ventilation ducts. Such enclosed spaces may be fully or partially enclosed. The objects may be indoors or outdoors.

The anti-microbial formulation of the present invention can be added to either aqueous or organic liquids to eliminate or reduce harmful microorganisms, to render them safe for use, to decontaminate, to purify or preserve, or to deliver the anti-microbial action/efficacy of the anti-microbial formulations of the present invention for a specific application.

The anti-microbial formulation of the present invention can be used to remove microorganisms from objects or enclosed spaces, or as a preservative to prevent future contamination and/or degradation by harmful microorganisms for objects such as paper, leather, paint, wood, wood products, fabrics (both natural and synthetic fibers), plastics, cellulosics, adhesives, waxes, paper and pulp slurries, carpets and carpet backings, and synthetic and natural latexes.

The objects and enclosed spaces where the anti-microbial formulation of the present invention can be applied or used include both on the surface and inside of a building, a body cavity of an animal, and a vehicle. Examples of a body cavity of an animal include, but are not limited to, an oral cavity, a sinus cavity, etc. Examples of vehicles include, but are not limited to, a car, a truck, a train, a boat, a ship, a plane, and a space craft. The anti-microbial formulation of the present invention can also be used or applied in the outdoor environment. Examples include the eradication of microorganisms on the exterior of buildings, sidewalks, stairs, railings, pavement, trees, poles and posts, curbs, roofs, pipes, playground, recreational and exercise equipment.

Gram positive, Gram negative, virus, mold, mildew, fungi, and spores are eradicated by the anti-microbial formulations of the present invention.

Procedures for the Preparation of the Anti-Microbial Formulations Contained in Tables 1-4 and 6-7

A 250 ml beaker equipped with a magnetic stir bar is charged first with water followed by the surfactant(s). The contents are stirred for 5 minutes at room temperature. Next the citric acid is added (if it is to be present in the formulation) and stirred at room temperature for 5 minutes. Hydrogen peroxide (either a 3% or a 30% solution or combination of both) is added (if present in the formulation) and stirred for 5 minutes at room temperature. Finally the peracetic acid is added and stirred at room temperature for 15 minutes. The pH is measured and the formulation is transferred to a high density polyethylene bottle for further testing and storage. No pressure build up in the bottle was noted on storage indicative that the anti-microbial formulations of the present invention are stable. In the above procedure, the hydrogen peroxide can be substituted with another peroxide or used in combination with another peroxide. Likewise the citric acid can be substituted with another acid or acid salt, or used in combination with another acid or acid salt. In a similar manner the peracetic acid can be substituted with another peracid or used in with another peracid. The anti-microbial formulations of the present invention can be used as prepared or diluted to about 1 to 1000, and preferably diluted up to about 1 to 500.

The preparation of Example #27 will demonstrate the above procedure.

A 250 ml beaker equipped with a magnetic stir bar is charged first with 35.00 g water followed by 9.00 g of Pluronic® L-31. The contents are stirred for 5 minutes at room temperature. 3.00 g of citric acid are added to the solution and it is stirred for 5 minutes at room temperature to form a homogeneous solution. Then 94.43 g of 3% active hydrogen peroxide solution are added and stirred for 5 minutes at room temperature. Finally, 8.57 g of 35% active peracetic acid are added and stirred for 15 minutes at room temperature. The clear homogenous solution has a pH of approximately 2 and was stored in a high density polyethylene bottle for further testing. No pressure build up in the bottle was noted on storage indicative of stable formulations. The anti-microbial formulation can be used as prepared or diluted as needed.

Procedures for the Preparation of the Anti-Microbial Formulations Contained in Table 5

Preparation of Example #58

A 250 ml beaker equipped with a magnetic stir bar is charged first with 10.37 g water followed by 3.00 g of Pluronic® L-31. The contents are stirred for 5 minutes at room temperature. To the solution is added 1.00 g of citric acid and stirred for 5 minutes at room temperature to form a homogeneous solution. Then 31.33 g of 3% active hydrogen peroxide solution are added and stirred while heating to 60-65 degrees C.° for 20 minutes. When the temperature of the solution reached about 40 degrees C.° it turned cloudy. After holding the cloudy formulation at 60-65 degrees centigrade for 20 minutes it was cooled to room temperature, at which point the solution was again clear and homogeneous. Then 4.30 g of 35% peracetic acid solution are added and the mixture is stirred for 15 minutes at room temperature. The clear homogenous solution has a pH of approximately 2 and was stored in a high density polyethylene bottle for further testing. No pressure build up in the bottle was noted on storage indng that the formulation is stable. The anti-microbial formulation can be used as prepared or diluted as needed.

Procedures for the Preparation of the Concentrated Anti-Microbial Formulations Contained in Table 11

In this section, it is demonstrated that anti-microbial formulations of the present invention can be prepared at high concentration and then diluted with water while still maintaining anti-microbial efficacy, stability and non-corrosiveness to ferrous metals. The following procedure was used to prepare a concentrate and further dilute it:

Preparation of Example #64

A 250 ml beaker equipped with a magnetic stir bar was charged with 8.03 grams water and 3.00 grams of Pluronic® L-43 ethylene oxide/propylene oxide triblock copolymer surfactant and stirred at room temperature for 5 minutes. Stirring was continued and 8.00 grams of citric acid was added and stirred for 5 minutes at room temperature. After dissolving the citric acid, 26.67 grams of 30% hydrogen peroxide was added and stirred at room temperature for 5 minutes. Stirring was continued and 4.30 grams of 35% peracetic acid was added and stirred for 15 minutes at room temperature. Total of 50 grams with a pH of about 2 or lower. The same procedure was used to prepare other concentrated anti-microbial formulations of the present invention and these compositions along with the composition of the above example #64 are set forth in Table 11.

Procedure for the Dilution of Concentrated Anti-Microbial Formulations Contained in Table 11

Preparation of Example 69

A 250 ml beaker equipped with a magnetic stir bar was charged with 45 grams of water and 5 grams of concentrated anti-microbial formulation of example #64 and stirred for 15 minutes at room temperature at a pH about 2 or lower.

Preparation of Example 70

In addition to diluting the formulation, other additives can be added to the formulation during the dilution procedure.

A 250 ml beaker equipped with a magnetic stir bar was charged with 43 grams of water and 2 grams of Pluronic® L-43. The contents are stirred for 5 minutes at room temperature. With continued stifling, 5.0 grams of concentrated anti-microbial formulation of example #64 were added and stirred for 15 minutes at room temperature at a pH about 2 or lower. Further dilutions are possible as needed for specific applications. The same procedure was used to prepare other concentrated anti-microbial formulations of the present invention and these compositions along with the composition of the above examples #69 and example #70 are in Table 12.

Alternative Preparation of t-Butyl Hydroperoxide Containing Anti-Microbial Formulations Preparation of Example #80

A 250 ml beaker equipped with a magnetic stir bar was charged with 16.70 grams water and 3.00 grams of Pluronic® L-43 ethylene oxide/propylene oxide triblock copolymer surfactant and stirred at room temperature for 5 minutes. Stirring was continued and 6.00 grams of citric acid was added and stirred for 5 minutes at room temperature. After dissolving the citric acid, 20.00 grams of 30% hydrogen peroxide was added and stirred at room temperature for 5 minutes. Stirring was continued, and 4.30 grams of 35% peracetic acid was added and stirred for 15 minutes at room temperature. Total of 50 grams with a pH of about 2 or lolr.

A 250 ml beaker equipped with a magnetic stir bar was charged with 44.30 grams of water and 0.70 grams of 70% t-butyl hydroperoxide and stirred 5 minutes at room temperature, and then 5 grams of the above concentrated anti-microbial formulation example was added and stirred for 15 minutes at room temperature. pH about 2 or lower. Table 13 contains formulations representative of the above preparation process. The isomers of butyl alcohol, the isomers of propyl alcohol, ethanol, or methanol can be used in place of the t-butyl hydroperoxide. Examples 84 and 85 in Table 13 use isopropyl alcohol in place of t-butyl hydroperoxide.

Alternative Process for the Preparation of T-Butyl Hydroperoxide Containing Anti-Microbial Formulations Preparation of Example 83

In an alternative process, the surfactant and citric acid are first heated to 60-65 degrees centigrade for 20 minutes with a small amount of hydrogen peroxide and cooled to room temperature before the remaining formulation ingredients are added. A 250 ml beaker equipped with a magnetic stir bar was charged with 16.70 grams 3% hydrogen peroxide and 3.00 grams of Pluronic® L-43 ethylene oxide/propylene oxide triblock copolymer surfactant and stirred at room temperature for 5 minutes. Stirring was continued and 6.00 grams of citric acid was added and stirred for 5 minutes at room temperature. After dissolving the citric acid, 20.00 grams of 30% hydrogen peroxide was added and stirred at room temperature for 5 minutes. Stirring was continued and 4.30 grams of 35% peracetic acid was added and stirred for 15 minutes at room temperature. Total of 50 grams with a pH of about 2 or lower. A 250 ml beaker equipped with a magnetic stir bar was charged with 42.90 grams of water and 2.10 grams of 70% t-butyl hydroperoxide and stirred 5 minutes at room temperature, and then 5 grams of the above concentrated anti-microbial formulation was added and stirred for 15 minutes at room temperature. pH about 2 or lower.

Example 83 in Table 13 was prepared in this manner with a preheating step.

TABLE 13

| Example # | % weight Surfactant and Type | % weight Citric Acid | % weight Hydrogen Peroxide | % weight Peracetic Acid | % weight t-butyl hydroperoxide |
|---|---|---|---|---|---|
| 80 | 0.6% Pluronic® L-31 | 1.2% | 1.2% | 0.3% | 1.0% |
| 81 | 0.6% Pluronic® L-31 | 1.2% | 1.2% | 0.3% | 3.0% |
| 82 | 0.6% Pluronic® L-31 | 1.2% | 1.2% | 0.3% | 5.0% |
| 83 | 0.6% Pluronic® L-31 | 1.2% | 1.2% | 0.3% | 3.0% |
| 84 | 5.7% Pluronic® L-31 | 2.85% | 2.85% | 2.85% | 4.55% isopropyl alcohol |
| 85 | 5.4% Pluronic® L-31 | 2.7% | 2.7% | 2.7% | 9.1% isopropyl alcohol |

The examples in Table 13 Are stable and Are non-corrosive to ferrous metals after contact for 2 weeks at room temperature.

Direct Preparation of Anti-microbial Formulations with Low Levels of Peracetic Acid Preparation of Example 86

A 250 ml beaker equipped with a magnetic stir bar is charged first with 43.07 g water followed by 3.00 g of Pluronic® L-43. The contents are stirred for 5 minutes at room temperature. To the solution is added 0.80 g of citric acid and it is stirred for 5 minutes at room temperature to form a homogeneous solution. Then 2.70 g of 30% active hydrogen peroxide solution are added and stirred for 5 minutes at room temperature. Finally, 0.43 g of 35% active peracetic acid is added and stirred for 15 minutes at room temperature. The clear homogenous solution has a pH of approximately 2 and was stored in a high density polyethylene bottle for further testing. No pressure build up in the bottle was noted on storage indicative of stable formulations. The anti-microbial formulation can be used as prepared or diluted as needed. Other compositions prepared by this process are contained in Table 14.

Example 89 in Table 14 was prepared by using an alternative preheating process described above

TABLE 14

| Example # | % weight Surfactant and Type | % weight Citric Acid | % weight Hydrogen Peroxide | % weight Peracetic Acid |
|---|---|---|---|---|
| 86 | 6.0% Pluronic® L-43 | 1.6% | 1.6% | 0.3% |
| 87 | 6.0% Pluronic® L-43 | 1.2% | 1.2% | 0.3% |
| 88 | 6.0% Pluronic® L-43 | 0.3% | 0.3% | 0.3% |
| 89 | 6.0% Pluronic® L-43 | 3.0% | 3.0% | 3.0% |

Preparation of Example 90

A 250 ml beaker equipped with a magnetic stir bar is charged first with 44.17 g water followed by 0.30 g of Pluronic® L-31. The contents are stirred for 5 minutes at room temperature. To the solution is added 0.60 g of citric acid and stirred for 5 minutes at room temperature to form a homogeneous solution. Then 2.00 g of 30% active hydrogen peroxide solution are added and stirred for 5 minutes at room temperature. Then 2.50 g of 91% aqueous isopropyl alcohol are added and stirred for 5 minutes at room temperature. Finally, 0.43 g of 35% active peracetic acid are added and stirred for 15 minutes at room temperature. The clear homogenous solution has a pH of approximately 2 and was stored in a high density polyethylene bottle for further testing. No pressure build up in the bottle was noted on storage indicative of stable formulations. No corrosion of a steel nail was observed after 2 weeks at room temperature.

Preparation of Example 91

A 250 ml beaker equipped with a magnetic stir bar is charged first with 13.90 g water followed by 3.00 g of Pluronic® L-31. The contents are stirred for 5 minutes at room temperature. To the solution is added 6.00 g of citric acid and stirred for 5 minutes at room temperature to form a homogeneous solution. Then 20.00 g of 30% active hydrogen peroxide solution are added and stirred for 5 minutes at room temperature. Finally, 7.14 g of 35% active peracetic acid are added and stirred for 15 minutes at room temperature. In a separate beaker equipped with a magnetic stir bar, 405.10 g water are added followed with stirring 45.20 g of the above solution at room temperature and stirred for 15 minutes. The clear homogenous solution has a pH of approximately 2 and was stored in a high density polyethylene bottle for further testing. No pressure build up in the bottle was noted on storage indicative of stable formulations. No corrosion of a steel nail was observed after 2 weeks at room temperature.

Preparation of Example 92

A 250 ml beaker equipped with a magnetic stir bar is charged first with 9.53 g water followed by 3.00 g of Pluronic® L-31. The contents are stirred for 5 minutes at room temperature. To the solution is added 7.00 g of citric acid and stirred for 5 minutes at room temperature to form a homogeneous solution. Then 23.33 g of 30% active hydrogen peroxide solution are added and stirred for 5 minutes at room temperature. Finally, 7.14 g of 35% active peracetic acid are added and stirred for 15 minutes at room temperature. In a separate beaker equipped with a magnetic stir bar, 405.08 g water are added followed with stirring 45.27 g of the above solution at room temperature and stirred for 15 minutes. The clear homogenous solution has a pH of approximately 2 and was stored in a high density polyethylene bottle for further testing. No pressure build up in the bottle was noted on storage indicative of stable formulations. No corrosion of a steel nail was observed after 2 weeks at room temperature.

Preparation of Example 93

A 250 ml beaker equipped with a magnetic stir bar is charged first with 6.10 g water followed by 6.00 g of Pluronic® L-31. The contents are stirred for 5 minutes at room temperature. To the solution is added 3.00 g of citric acid and stirred for 5 minutes at room temperature to form a homogeneous solution. Then 62.66 g of 3% active hydrogen peroxide and 3.74 g of 30% active hydrogen peroxide solution are added and stirred for 5 minutes at room temperature. Then 9.95 g of 91% aqueous isopropyl alcohol are added and stirred for 5 minutes at room temperature. Finally, 8.60 g of 35% active peracetic acid are added and stirred for 15 minutes at room temperature. The clear homogenous solution has a pH of approximately 2 and was stored in a high density polyethylene bottle for further testing. No pressure build up in the bottle was noted on storage indicative of stable formulations. No corrosion of a steel nail was observed after 2 weeks at room temperature.

Preparation of Example 94

A 250 ml beaker equipped with a magnetic stir bar is charged first with 16.70 g water followed by 3.00 g of Pluronic® L-31. The contents are stirred for 5 minutes at room temperature. To the solution is added 6.00 g of citric acid and stirred for 5 minutes at room temperature to form a homogeneous solution. Then 20.00 g of 30% active hydrogen peroxide solution are added and stirred for 5 minutes at room temperature. Finally, 4.30 g of 35% active peracetic acid are added and stirred for 15 minutes at room temperature. In a separate beaker equipped with a magnetic stir bar, 43.00 g water and 2.00 g 91% aqueous isopropyl alcohol are added followed with stirring 5.00 g of the above solution at room temperature and stirred for 15 minutes. The clear homogenous solution has a pH of approximately 2 and was stored in a high density polyethylene bottle for further testing. No pressure build up in the bottle was noted on storage indicative of stable formulations.

Preparation of Example 95

A 250 ml beaker equipped with a magnetic stir bar is charged first with 16.70 g water followed by 3.00 g of Pluronic® L-31. The contents are stirred for 5 minutes at room temperature. To the solution is added 6.00 g of citric acid and stirred for 5 minutes at room temperature to form a homogeneous solution. Then 20.00 g of 30% active hydrogen peroxide solution are added and stirred for 5 minutes at room temperature. Finally, 4.30 g of 35% active peracetic acid are added and stirred for 15 minutes at room temperature. In a separate beaker equipped with a magnetic stir bar, 43.00 g water and 2.00 g Pluronic® L-31 are added followed with stifling 5.00 g of the above solution at room temperature and stirred for 15 minutes. The clear homogenous solution has a pH of approximately 2 and was stored in a high density polyethylene bottle for further testing. No pressure build up in the bottle was noted on storage indicative of stable formulations.

Preparation of Example 96

A 250 ml beaker equipped with a magnetic stir bar is charged first with 16.70 g water followed by 3.00 g of Pluronic® L-31. The contents are stirred for 5 minutes at room temperature. To the solution is added 6.00 g of citric acid and stirred for 5 minutes at room temperature to form a homogeneous solution. Then 20.00 g of 30% active hydrogen peroxide solution are added and stirred for 5 minutes at room temperature. Finally, 4.30 g of 35% active peracetic acid are added and stirred for 15 minutes at room temperature. In a separate beaker equipped with a magnetic stir bar, 21.50 g water and 1.00 g butyl cellusolve are added followed with stirring 2.50 g of the above solution at room temperature and stirred for 15 minutes. The clear homogenous solution has a pH of approximately 2 and was stored in a high density polyethylene bottle for further testing. No pressure build up in the bottle was noted on storage indicative of stable formulations.

Preparation of Example 97

A 250 ml beaker equipped with a magnetic stir bar is charged first with 29.60 g of 30% active hydrogen peroxide aqueous solution followed by 8.80 g of citric acid and stirred for 5 minutes at room temperature to form a homogeneous solution. Then 3.00 g of Pluronic® L-31 are added and stirred for 5 minutes at room temperature to form a homogeneous solution. Finally, 8.60 g of 35% active peracetic acid are added and stirred for 15 minutes at room temperature. In a separate beaker equipped with a magnetic stir bar 180.27 g water containing 100 ppm of sodium pyrophosphate are added followed with stirring 20.05 g of the above solution at room temperature and stirred for 15 minutes. The clear homogenous solution has a pH of approximately 2 and was stored in a high density polyethylene bottle for further testing. No pressure build up in the bottle was noted on storage indicative of stable formulations. No corrosion of a steel nail was observed after 2 weeks at room temperature.

Preparation of Example 98

A 250 ml beaker equipped with a magnetic stir bar is charged first with 29.60 g of 30% active hydrogen peroxide aqueous solution followed by 8.80 g of citric acid and stirred for 5 minutes at room temperature to form a homogeneous solution. Then 3.00 g of Pluronic® L-31 are added and stirred for 5 minutes at room temperature to form a homogeneous solution. Finally, 8.60 g of 35% active peracetic acid are added and stirred for 15 minutes at room temperature. In a separate beaker equipped with a magnetic stir bar 85.56 g water containing 100 ppm of sodium pyrophosphate and 4.47 g of 91% aqueous isopropyl alcohol are added followed with stirring 10.04 g of the above solution at room temperature and stirred for 15 minutes. The clear homogenous solution has a pH of approximately 2 and was stored in a high density polyethylene bottle for further testing. No pressure build up in the bottle was noted on storage indicative of stable formulations. No corrosion of a steel nail was observed after 2 weeks at room temperature.

Preparation of Example 99

A 250 ml beaker equipped with a magnetic stir bar is charged first with 29.60 g of 30% active hydrogen peroxide aqueous solution followed by 8.80 g of citric acid and stirred for 5 minutes at room temperature to form a homogeneous solution. Then 3.00 g of Pluronic® L-31 are added and stirred for 5 minutes at room temperature to form a homogeneous solution. Finally, 8.60 g of 35% active peracetic acid are added and stirred for 15 minutes at room temperature. In a separate beaker equipped with a magnetic stir bar 90.16 g distilled water containing 100 ppm of sodium pyrophosphate are added followed with stirring 10.00 g of the above solution at room temperature and stirred for 15 minutes. The clear homogenous solution has a pH of approximately 2 and was stored in a high density polyethylene bottle for further testing. No pressure build up in the bottle was noted on storage indicative of stable formulations. No corrosion of a steel nail was observed after 2 weeks at room temperature.

Preparation of Example 100

A 250 ml beaker equipped with a magnetic stir bar is charged first with 29.60 g of 30% active hydrogen peroxide aqueous solution followed by 8.80 g of citric acid and stirred for 5 minutes at room temperature to form a homogeneous solution. Then 3.00 g of Pluronic® L-31 are added and stirred for 5 minutes at room temperature to form a homogeneous solution. Finally, 8.60 g of 35% active peracetic acid are added and stirred for 15 minutes at room temperature. In a separate beaker equipped with a magnetic stir bar 81.61 g water containing 100 ppm of sodium pyrophosphate, 4.02 g Pluronic® L-121 and 4.46 g of 91% aqueous isopropyl alcohol are added followed with stifling 9.89 g of the above solution at room temperature and stirred for 15 minutes. The white appearing emulsion has a pH of approximately 2 and was stored in a high density polyethylene bottle for further testing. No pressure build up in the bottle was noted on storage indicative of stable formulations. No corrosion of a steel nail was observed after 2 weeks at room temperature.

Preparation of Example 101

A 250 ml Erlenmeyer flask equipped with a magnetic stir bar is charged first with 91.89 g of water which contains 100 ppm of sodium pyrophosphate followed by 1.49 g of Pluronic® F-87 surfactant and stirred for 25 minutes at room temperature to form a homogeneous solution. Then 4.41 g of citric acid was added and stirred for 5 minutes at room temperature to form a homogeneous solution. Then 148.03 g of 3% hydrogen peroxide was added and stirred for 5 minutes at room temperature to form a homogeneous solution. Finally, 4.37 g of 35% active peracetic acid are added and stirred for 15 minutes at room temperature. The clear homogenous solution has a pH of approximately 1.3 and was stored in a high density polyethylene bottle for further testing. No pressure build up in the bottle was noted on storage indicative of a stable formulation. No corrosion of a steel nail was observed after 2 weeks at room temperature.

Preparation of Example 102

A 250 ml Erlenmeyer flask equipped with a magnetic stir bar is charged first with 91.85 g of water which contains 100 ppm of sodium pyrophosphate followed by 1.52 g of Pluronic® F-108 surfactant and stirred for 25 minutes at room temperature to form a homogeneous solution. Then 4.39 g of citric acid was added and stirred for 5 minutes at room temperature to form a homogeneous solution. Then 150.17 g of 3% hydrogen peroxide was added and stirred for 5 minutes at room temperature to form a homogeneous solution. Finally, 4.34 g of 35% active peracetic acid are added and stirred for 15 minutes at room temperature. The clear homogenous solution has a pH of approximately 1.3 and was stored in a high density polyethylene bottle for further testing. No pressure build up in the bottle was noted on storage indicative of a stable formulation. No corrosion of a steel nail was observed after 2 weeks at room temperature.

PREPARATION OF EXAMPLES 103, 104, 105

A 250 ml beaker equipped with a magnetic stir bar is charged first with 29.67 g of 30% hydrogen peroxide followed by 3.01 g of Pluronic® F-108 surfactant and stirred for 25 minutes at room temperature to form a homogeneous solution. Then 8.86 g of citric acid was added and stirred for 5 minutes at room temperature to form a homogeneous solution. Finally, 8.64 g of 35% active peracetic acid are added and stirred for 15 minutes at room temperature. The clear homogenous solution has a pH of approximately 1.3 and was stored in a high density polyethylene bottle for further testing. No pressure build up in the bottle was noted on storage indicative of a stable formulation. No corrosion of a steel nail was observed after 2 weeks at room temperature.

Preparation of Example 104

In a 250 ml beaker 85.67 g water, 10.02 g of the formulation of Example 103 and 4.43 g Of 91% aqueous isopropyl alcohol are combined and stirred at room temperature for 10 minutes.

Preparation of Example 105

In a 250 ml beaker 81.23 g water, 10.06 g of the formulation of Example 103 and 8.85 g Of 91% aqueous isopropyl alcohol are combined and stirred at room temperature for 10 minutes.

Preparation of Example 106

A 250 ml Erlenmeyer flask equipped with a magnetic stir bar is charged first with 93.05 g of water followed by 0.25 g of Pluronic® F-1 08 surfactant and stirred for 20 minutes at room temperature to form a homogeneous solution. Then 4.41 g of citric acid was added and stirred for 5 minutes at room temperature to form a homogeneous solution. Then 148.01 g of 3% hydrogen peroxide was added and stirred for 5 minutes at room temperature to form a homogeneous solution. Finally, 4.49 g of 35% active peracetic acid are added and stirred for 15 minutes at room temperature. The clear homogenous solution has a pH of approximately 1.5 and was stored in a high density polyethylene bottle for further testing. No pressure build up in the bottle was noted on storage indicative of a stable formulation. No corrosion of a steel nail was observed after 2 weeks at room temperature.

Preparation of Example 107

A 250 ml Erlenmeyer flask equipped with a magnetic stir bar is charged first with 92.84 g of water followed by 0.51 g of Pluronic® F-1 08 surfactant and stirred for 20 minutes at room temperature to form a homogeneous solution. Then 4.39 g of citric acid was added and stirred for 5 minutes at room temperature to form a homogeneous solution. Then 148.00 g of 3% hydrogen peroxide was added and stirred for 5 minutes at room temperature to form a homogeneous solution. Finally, 4.50 g of 35% active peracetic acid are added and stirred for 15 minutes at room temperature. The clear homogenous solution has a pH of approximately 1.5 and was stored in a high density polyethylene bottle for further testing. No pressure build up in the bottle was noted on storage indicative of a stable formulation. No corrosion of a steel nail was observed after 2 weeks at room temperature.

Preparation of Example 108

A 250 ml Erlenmeyer flask equipped with a magnetic stir bar is charged first with 93.05 g of water followed by 0.26 g of Pluronic® F-38 surfactant and stirred for 20 minutes at room temperature to form a homogeneous solution. Then 4.40 g of citric acid was added and stirred for 5 minutes at room temperature to form a homogeneous solution. Then 148.03 g of 3% hydrogen peroxide was added and stirred for 5 minutes at room temperature to form a homogeneous solution. Finally, 4.30 g of 35% active peracetic acid are added and stirred for 15 minutes at room temperature. The clear homogenous solution has a pH of approximately 1.5 and was stored in a high density polyethylene bottle for further testing. No pressure build up in the bottle was noted on storage indicative of a stable formulation. No corrosion of a steel nail was observed after 2 weeks at room temperature.

Preparation of Example 109

A 250 ml Erlenmeyer flask equipped with a magnetic stir bar is charged first with 45.08 g of water and 48.00 g of 3% hydrogen peroxide followed by 0.26 g of Pluronic® F-38 surfactant and stirred for 20 minutes at room temperature to form a homogeneous solution. Then 4.44 g of citric acid was added and stirred with heating. The homogeneous solution was held at 60 to 65 degrees centigrade for 20 minutes and then cooled to 35 degrees centigrade. Then 48.39 g of water and 100.05 g of 3% hydrogen peroxide were added and stirred for 5 minutes at room temperature to form a homogeneous solution. Finally, 4.34 g of 35% active peracetic acid are added and stirred for 15 minutes at room temperature. The clear homogenous solution has a pH of approximately 1.5 and was stored in a high density polyethylene bottle for further testing. No pressure build up in the bottle was noted on storage indicative of a stable formulation. No corrosion of a steel nail was observed after 2 weeks at room temperature, Preparation of Example 110

A 250 ml Erlenmeyer flask equipped with a magnetic stir bar is charged first with 93.05 g of water containing 100 ppm of sodium pyrophosphate followed by 0.27 g of Pluronic® F-38 surfactant and stirred for 20 minutes at room temperature to form a homogeneous solution. Then 4.41 g of citric acid was added and stirred for 5 minutes at room temperature to form a homogeneous solution. Then 148.08 g of 3% hydrogen peroxide was added and stirred for 5 minutes at room temperature to form a homogeneous solution. Finally, 4.34 g of 35% active peracetic acid are added and stirred for 15 minutes at room temperature. The clear homogenous solution has a pH of approximately 1.5 and was stored in a high density polyethylene bottle for further testing. No pressure build up in the bottle was noted on storage indicative of a stable formulation. No corrosion of a steel nail was observed after 2 weeks at room temperature.

Preparation of Example 111

A 250 ml Erlenmeyer flask equipped with a magnetic stir bar is charged first with 93.05 g of water containing 100 ppm of sodium pyrophosphate followed by 0.27 g of Pluronic® F-88 surfactant and stirred for 20 minutes at room temperature to form a homogeneous solution. Then 4.41 g of citric acid was added and stirred for 5 minutes at room temperature to form a homogeneous solution. Then 148.08 g of 3% hydrogen peroxide was added and stirred for 5 minutes at room temperature to form a homogeneous solution. Finally, 4.34 g of 35% active peracetic acid are added and stirred for 15 minutes at room temperature. The clear homogenous solution has a pH of approximately 1.5 and was stored in a high density polyethylene bottle for further testing. No pressure build up in the bottle was noted on storage indicative of a stable formulation. No corrosion of a steel nail was observed after 2 weeks at room temperature.

Preparation of Example 112

A 250 ml Erlenmeyer flask equipped with a magnetic stir bar is charged first with 93.05 g of water containing 300 ppm of sodium pyrophosphate followed by 0.25 g of Pluronic® F-38 surfactant and stirred for 20 minutes at room temperature to form a homogeneous solution. Then 4.42 g of citric acid was added and stirred for 5 minutes at room temperature to form a homogeneous solution. Then 148.08 g of 3% hydrogen peroxide was added and stirred for 5 minutes at room temperature to form a homogeneous solution. Finally, 4.32 g of 35% active peracetic acid are added and stirred for 15 minutes at room temperature. The clear homogenous solution has a pH of approximately 1.5 and was stored in a high density polyethylene bottle for further testing. No pressure build up in the bottle was noted on storage indicative of a stable formulation. No corrosion of a steel nail was observed after 2 weeks at room temperature.

Preparation of Example 113

A 250 ml Erlenmeyer flask equipped with a magnetic stir bar is charged first with 93.05 g of water containing 300 ppm of sodium pyrophosphate followed by 0.25 g of Pluronic® F-88 surfactant and stirred for 20 minutes at room temperature to form a homogeneous solution. Then 4.41 g of citric acid was added and stirred for 5 minutes at room temperature to form a homogeneous solution. Then 148.13 g of 3% hydrogen peroxide was added and stirred for 5 minutes at room temperature to form a homogeneous solution. Finally, 4.33 g of 35% active peracetic acid are added and stirred for 15 minutes at room temperature. The clear homogenous solution has a pH of approximately 1.5 and was stored in a high density polyethylene bottle for further testing. No pressure build up in the bottle was noted on storage indicative of a stable formulation. No corrosion of a steel nail was observed after 2 weeks at room temperature.

Preparation of Example 114

A 250 ml Erlenmeyer flask equipped with a magnetic stir bar is charged first with 83.1 Og of water containing 300 ppm of sodium pyrophosphate followed by 0.26 g of Pluronic® F-38 surfactant and stirred for 20 minutes at room temperature to form a homogeneous solution. Then 4.43 g of citric acid was added and stirred for 5 minutes at room temperature to form a homogeneous solution. Then 148.00 g of 3% hydrogen peroxide was added and stirred for 5 minutes at room temperature to form a homogeneous solution. Then, 4.30 g of 35% active peracetic acid are added and stirred for 10 minutes at room temperature. Finally, 10.05 g of denatured ethanol was added and stirred for 15 minutes at room temperature. The clear homogenous solution has a pH of approximately 1.5 and was stored in a high density polyethylene bottle for further testing. No pressure build up in the bottle was noted on storage indicative of a stable formulation. No corrosion of a steel nail was observed after 2 weeks at room temperature.

Preparation of Example 115

A 250 ml Erlenmeyer flask equipped with a magnetic stir bar is charged first with 73.07 g of water containing 300 ppm of sodium pyrophosphate followed by 0.25 g of Pluronic® F-38 surfactant and stirred for 20 minutes at room temperature to form a homogeneous solution. Then 4.41 g of citric acid was added and stirred for 5 minutes at room temperature to form a homogeneous solution. Then 148.05 g of 3% hydrogen peroxide was added and stirred for 5 minutes at room temperature to form a homogeneous solution. Then, 4.31 g of 35% active peracetic acid are added and stirred for 10 minutes at room temperature. Finally, 20.04 g of denatured ethanol was added and stirred for 15 minutes at room temperature. The clear homogenous solution has a pH of approximately 1.5 and was stored in a high density polyethylene bottle for further testing. No pressure build up in the bottle was noted on storage indicative of a stable formulation. No corrosion of a steel nail was observed after 2 weeks at room temperature.

Preparation of Example 116

This formulation is an example of a high surfactant level antimicrobial with a low water content. An approximately 60 ml glass was charged with 0.09 g of 30% hydrogen peroxide, 0.09 g of 35% peracetic acid and 0.03 g of citric acid. The mixture was manually stirred at room temperature with a disposable plastic pipette for 5 minutes to form a homogeneous solution. Then 9.79 g of Pluronic® L-31 was added and also manually stirred at room temperature with a disposable plastic pipette for 5 minutes to form a homogeneous solution. The solution had a pH of about 3.5 and was stored in a 30 ml plastic bottle. The formulation has the following composition: 97.9% Pluronic® L-31 surfactant, 0.3% citric acid, 0.27% hydrogen peroxide, 0.32% peracetic acid. Using other Pluronic® surfactants for example such as P-65 or P-94 or F-38 or F-88 provides a means of forming a high solids, high surfactant antimicrobial formulation which is in a paste or solid form.

Preparation of Example 117

This formulation is an example of a high surfactant level antimicrobial with a low water content. An approximately 60 ml glass was charged with 0.09 g of 30% hydrogen peroxide, 0.09 g of 35% peracetic acid and 0.03 g of citric acid. The mixture was manually stirred at room temperature with a disposable plastic pipette for 5 minutes to form a homogeneous solution. Then 9.79 g of Pluronic® L-121 was added and also manually stirred at room temperature with a disposable plastic pipette for 5 minutes to form a solution. This solution has a slight white tint consistent with the water insolubility of Pluronic® L-121. The solution had a pH of about 3.5 and was stored in a 30 ml plastic bottle. The formulation has the following composition: 97.9% Pluronic® L-121 surfactant, 0.3% citric acid, 0.27% hydrogen peroxide, 0.32% peracetic acid.

Preparation of Example 118

This formulation is an example of a high peracetic acid antimicrobial. A 250 ml beaker equipped with a magnetic stir bar was charged with 11.01 g of water containing 100 ppm sodium pyrophosphate, 0.05 g Pluronic® F-38 and 1.51 g citric acid. The mixture was stirred for 10 minutes at room temperature to form a homogeneous solution. Then 31.35 g of 3% hydrogen peroxide and 1.89 g of 30% hydrogen peroxide were added and stirred for 10 minutes at room temperature. Finally 4.32 g of 35% peracetic acid are added and stirred 15 minutes at room temperature. The solution had a pH of about 1.0 and was stored in two 30 ml plastic bottles. The formulation has the following composition: 0.1% Pluronic® F-38 surfactant, 3.0% citric acid, 3.0% hydrogen peroxide, 3.0% peracetic acid.

Preparation of Example 119

This formulation is an example of a t-butyl hydroperoxide containing antimicrobial. A 500 ml Erlenmeyer flask equipped with a magnetic stir bar was charged with 82.35 g of water containing 100 ppm sodium pyrophosphate, 0.25 g Pluronic® F-38 and 4.43 g citric acid. The mixture was stirred for 10 minutes at room temperature to form a homogeneous solution. Then 148.07 g of 3% hydrogen peroxide are added and stirred for 10 minutes at room temperature. Then 4.39 g of 35% peracetic acid are added and stirred 15 minutes at room temperature. Finally 10.89 g Of 70% t-butyl hydroperoxide are added and stirred. A slightly hazy solution becomes clear after about 15 minutes of stifling at room temperature. The solution had a pH of about 1.7 and was stored in a 250 ml plastic bottle. The formulation has about the following composition: 0.1% Pluronic® F-38 surfactant, 1.8% citric acid, 1.8% hydrogen peroxide, 0.6% peracetic acid, 3.0% t-butyl hydroperoxide.

Time to Kill *Staphylococcus aureus* and *Escherichia coli* Results for Examples 47, 48, 80, 81, 90 through 96 and 98 and 99

This approach to examine bactericidal activity involves exposing a bacterial isolate (such as *Staphylococcus aureus* or *Escherichia coli*) to a concentration of antimicrobial in a broth medium at any desired dilution and then measuring the rate of killing over a specified period of time. By this time-kill analysis, Samples are taken from the antimicrobial-broth solution immediately after the inoculum was added and at regular intervals thereafter. For example, a typical time sequence might be aliquots to be taken at 0, 1, 3, 5, and 10 minutes, etc., for culture. Any time sequence desired can obviously be substituted depending upon the purpose of the experiment. Each time-sample is then plated onto agar plates which are, in turn, incubated overnight at 35 C and observed for growth. Following incubation, the colonies are counted and expressed as CFU's/ml (colony-forming units per milliliter). These can then be compared to the original inoculum (0 control) in order to determine the logarithmic decrease in growth and therefore the efficacy of the antimicrobial formulation. In these tests about 10 to the 6th cfu were used and the example formulations were tested after a 1 to 2 dilution with a 4% human protein broth. The results are given below for the specific examples. A "0" rating in the following tables indicates that all the microorganisms were killed at the time indicated and is indicative of a very efficacious antimicrobial.

Example 47

6% Pluronic® L-31, 3% citric acid, 3% hydrogen peroxide, 3% peracetic acid—diluted 1:2 with 4% protein serum. The results exemplify outstanding time to kill.

| Time (min) | S. aureus (cfu) | E. coli (cfu) |
|---|---|---|
| 1 | 0 | 0 |
| 3 | 0 | 0 |
| 5 | 0 | 0 |
| 10 | 0 | 0 |

Example 48

6% Pluronic® L-43, 3% citric acid, 3% hydrogen peroxide, 3% peracetic acid—diluted 1:2 with 4% protein serum. The results exemplify outstanding time to kill.

| Time (min) | S. aureus (cfu) | E. coli (cfu) |
|---|---|---|
| 1 | 0 | 0 |
| 3 | 0 | 0 |
| 5 | 0 | 0 |
| 10 | 0 | 0 |

Example 80

6% Pluronic® L-43 1.2% citric acid, 1.2% hydrogen peroxide, 0.3% peracetic acid, 1% TBHP: diluted (1:2) with 4% protein serum. The results exemplify outstanding time to kill.

| Time (min) | S. aureus (cfu) | E. coli (cfu) |
|---|---|---|
| 1 | 0 | 0 |
| 3 | 0 | 0 |
| 5 | 0 | 0 |
| 10 | 0 | 0 |

Example 81

6% Pluronic® L-43 1.2% citric acid, 1.2% hydrogen peroxide, 0.3% peracetic acid, 3% TBHP: diluted (1:2) with 4% protein serum. The results exemplify outstanding time to kill.

| Time (min) | S. aureus (cfu) | E. coli (cfu) |
|---|---|---|
| 1 | 0 | 0 |
| 3 | 0 | 0 |
| 5 | 0 | 0 |
| 10 | 0 | 0 |

Example 90

0.6% Pluronic® L-31, 1.2% citric acid, 1.2% hydrogen peroxide, 0.6% peracetic acid, 4.55% isopropanol—diluted 1:2 with 4% protein serum. The results exemplify outstanding time to kill.

| Time (min) | S. aureus (cfu) | E. coli (cfu) |
|---|---|---|
| 1 | 0 | 0 |
| 3 | 0 | 0 |
| 5 | 0 | 0 |
| 10 | 0 | 0 |

Example 91

0.6% Pluronic® L-31, 1.2% citric acid, 1.2% hydrogen peroxide, 0.5% peracetic acid,—diluted 1:2 with 4% protein serum. The results exemplify outstanding time to kill.

| Time (min) | S. aureus (cfu) | E. coli (cfu) |
|---|---|---|
| 1 | 0 | 0 |
| 3 | 0 | 0 |
| 5 | 0 | 0 |
| 10 | 0 | 0 |

Example 92

0.6% Pluronic® L-31, 1.4% citric acid, 1.4% hydrogen peroxide, 0.5% peracetic acid,—diluted 1:2 with 4% protein serum. The results exemplify outstanding time to kill.

| Time (min) | S. aureus (cfu) | E. coli (cfu) |
|---|---|---|
| 1 | 0 | 0 |
| 3 | 0 | 0 |
| 5 | 0 | 0 |
| 10 | 0 | 0 |

Example 93

6% Pluronic® L-31, 3% citric acid, 3% hydrogen peroxide, 3% peracetic acid, 9% isopropanol—diluted 1:2 with 4% protein serum. The results exemplify outstanding time to kill.

| Time (min) | S. aureus (cfu) | E. coli (cfu) |
|---|---|---|
| 1 | 0 | 0 |
| 3 | 0 | 0 |
| 5 | 0 | 0 |
| 10 | 0 | 0 |

Example 94

0.6% Pluronic® L-31, 1.2% citric acid, 1.2% hydrogen peroxide, 0.3% peracetic acid, 4% isopropyl alcohol—diluted 1:2 with 4% protein serum. The results exemplify outstanding time to kill

| Time (min) | S. aureus (cfu) | E. coli (cfu) |
|---|---|---|
| 1 | 0 | 0 |
| 5 | 0 | 0 |
| 10 | 0 | 0 |

Example 95

0.6% Pluronic® L-31, 1.2% citric acid, 1.2% hydrogen peroxide, 0.3% peracetic acid, 4% Pluronic® L-121 (from concentrate diluted 1 to 10),—diluted 1:2 with 4% protein serum. The results exemplify outstanding time to kill.

| Time (min) | S. aureus (cfu) | E. coli (cfu) |
|---|---|---|
| 1 | 0 | 1 |
| 5 | 0 | 0 |
| 10 | 0 | 0 |

Example 96

0.6% Pluronic® L-31, 1.2% citric acid, 1.2% hydrogen peroxide, 0.3% peracetic acid, 4% butyl cellusolve (from concentrate diluted 1 to 10),—diluted 1:2 with 4% protein serum. The results exemplify outstanding time to kill.

| Time (min) | S. aureus (cfu) | E. coli (cfu) |
|---|---|---|
| 1 | 3 | 0 |
| 5 | 0 | 0 |
| 10 | 0 | 0 |

Example 98

0.6% Pluronic® L-31, 1.76% citric acid, 1.78% hydrogen peroxide, 0.6% peracetic acid, 4% isopropanol with water containing 100 ppm sodium pyrophosphate—diluted 1:2 with 4% protein serum. The results exemplify outstanding time to kill

| Time (min) | S. aureus (cfu) | E. coli (cfu) |
|---|---|---|
| 1 | 0 | 0 |
| 5 | 0 | 0 |
| 10 | 0 | 0 |

Example 99

0.6% Pluronic® L-31, 1.76% citric acid, 1.78% hydrogen peroxide, 0.6% peracetic acid, with distilled water containing 100 ppm sodium pyrophosphate—diluted 1:2 with 4% protein serum. The results exemplify outstanding time to kill.

| Time (min) | S. aureus (cfu) | E. coli (cfu) |
|---|---|---|
| 1 | 0 | 0 |
| 5 | 0 | 0 |
| 10 | 0 | 0 |

The Time to Kill test was repeated using a very high microorganism challenging load with the antimicrobial of Example 99-0.6% Pluronic® L-31, 1.76% citric acid, 1.78% hydrogen peroxide, 0.6% peracetic acid, with distilled water containing 100 ppm sodium pyrophosphate—diluted 1:2 with 4% protein serum and challenged with a very high microorganism load of 10 to the ninth. The results again exemplify outstanding time to kill even with the much more demanding challenge.

| Time (min) | S. aureus (cfu) | E. coli (cfu) |
|---|---|---|
| 1 | 0 | 0 |
| 5 | 0 | 0 |
| 10 | 0 | 0 |

The Time to Kill test was repeated using a broad spectrum of very difficult to kill microorganisms with the antimicrobial of Example 99.

| Microorganism | 1 minute Time to Kill | 5 minute Time to Kill | 10 minute Time to Kill |
|---|---|---|---|
| Pseudomonas aeruginosa | 0 | 0 | 0 |
| Methicillan resistant Staphylococcus aureus | 0 | 0 | 0 |
| Acinetobacter bauminii | Significant growth | 0 | 0 |
| Salmonella cholerasuis | Significant growth | 0 | 0 |
| Vancomycin resistant Enterococci | Some growth | 0 | 0 |
| E. coli AMPC | 0 | 0 | 0 |
| Methicillan resistant S. Epidermis | 0 | 0 | 0 |
| ESBL Klebsiella pneumoniae | 0 | 0 | 0 |

These results indicate that the antimicrobial of the present invention has superior performance against very difficult to kill/resistant microorganisms.

Example 108

0.1% Pluronic® F-38, 1.76% citric acid, 1.78% hydrogen peroxide, 0.6% peracetic acid,—diluted 1:2 with 4% protein serum. The results exemplify outstanding time to kill.

| Microorganism | 1 minute Time to Kill | 5 minute Time to Kill | 10 minute Time to Kill |
|---|---|---|---|
| E. coli | 0 | 0 | 0 |
| Staphylococcus aureus | 0 | 0 | 0 |
| Acinetobacter bauminii | 0 | 0 | 0 |
| Salmonella cholerasuis | 0 | 0 | 0 |

Example 109

0.1% Pluronic® F-38, 1.76% citric acid, 1.78% hydrogen peroxide, 0.6% peracetic acid with a preheating process preparation step,—diluted 1:2 with 4% protein serum. The results exemplify outstanding time to kill.

| Microorganism | 1 minute Time to Kill | 5 minute Time to Kill | 10 minute Time to Kill |
|---|---|---|---|
| E. coli | 0 | 0 | 0 |
| Staphylococcus aureus | 0 | 0 | 0 |
| Acinetobacter bauminii | 0 | 0 | 0 |
| Salmonella cholerasuis | 0 | 0 | 0 |

Example 109

0.1% Pluronic® F-38, 1.76% citric acid, 1.78% hydrogen peroxide, 0.6% peracetic acid with a preheating process preparation step,—diluted 1:2 with 4% protein serum. The results exemplify outstanding time to kill.

| Microorganism | 1 minute Time to Kill | 5 minute Time to Kill | 10 minute Time to Kill |
|---|---|---|---|
| E. coli | 0 | 0 | 0 |
| Staphylococcus aureus | 0 | 0 | 0 |
| Acinetobacter bauminii | 0 | 0 | 0 |
| Salmonella cholerasuis | 0 | 0 | 0 | a. Table 15 contains a description and the characteristics of preferred surfactants of anti-microbial formulations of the present invention.

TABLE 15

| BASF Designation | Approximate molecular light of the propylene oxide/ethylene oxide block copolymer | Approximate molecular light of the propylene oxide block | Approximate % of ethylene oxide content in the propylene oxide/ethylene oxide block copolymer |
|---|---|---|---|
| Pluronic ® L-31 | 1100 | 950 | 10 |
| Pluronic ® L-61 | 2000 | 1750 | 10 |
| Pluronic ® L-81 | 2750 | 2250 | 10 |
| Pluronic ® L-101 | 3800 | 3250 | 10 |
| Pluronic ® L-121 | 4400 | 4000 | 10 |
| Pluronic ® L-42 | 1630 | 1200 | 20 |
| Pluronic ® L-62 | 2500 | 1750 | 20 |
| Pluronic ® L-72 | 2750 | 2050 | 20 |
| Pluronic ® L-92 | 3650 | 2750 | 20 |
| Pluronic ® L-122 | 5000 | 4000 | 20 |
| Pluronic ® L-43 | 1850 | 1200 | 30 |
| Pluronic ® L-63 | 2650 | 1750 | 30 |
| Pluronic ® P-103 | 4950 | 3250 | 30 |
| Pluronic ® P-123 | 5750 | 4000 | 30 |
| Pluronic ® L-44 | 2200 | 1200 | 40 |
| Pluronic ® L-64 | 2900 | 1750 | 40 |
| Pluronic ® P-84 | 4200 | 2250 | 40 |
| Pluronic ® P-94 | 5100 | 2750 | 40 |
| Pluronic ® P-104 | 5850 | 3250 | 40 |
| Pluronic ® L-35 | 1900 | 950 | 50 |
| Pluronic ® P-65 | 3400 | 1750 | 50 |
| Pluronic ® P-75 | 4150 | 2050 | 50 |
| Pluronic ® P-85 | 4600 | 2250 | 50 |
| Pluronic ® P-105 | 6500 | 3250 | 50 |
| Pluronic ® F-77 | 6600 | 2050 | 70 |
| Pluronic ® F-87 | 7700 | 2250 | 70 |
| Pluronic ® F-127 | 12500 | 4000 | 70 |
| Pluronic ® F-38 | 5000 | 950 | 80 |
| Pluronic ® F-68 | 8350 | 1750 | 80 |
| Pluronic ® F-88 | 10800 | 2250 | 80 |
| Pluronic ® F-98 | 13500 | 2750 | 80 |
| Pluronic ® F-108 | 14000 | 3250 | 80 |
| Pluronic ® 17R1 | 1950 | 1700 | 10 |
| Pluronic ® 25R1 | 2800 | 2500 | 10 |
| Pluronic ® 31R1 | 3200 | 3100 | 10 |
| Pluronic ® 17R2 | 2100 | 1700 | 20 |
| Pluronic ® 25R2 | 3120 | 2500 | 20 |
| Pluronic ® 31R2 | 3400 | 3100 | 20 |
| Pluronic ® 12R3 | 1560 | 1200 | 30 |
| Pluronic ® 17R4 | 2700 | 1700 | 40 |
| Pluronic ® 22R4 | 3080 | 2200 | 40 |
| Pluronic ® 25R4 | 4500 | 2500 | 40 |
| Pluronic ® 31R4 | 4300 | 3100 | 40 |
| Pluronic ® 10R5 | 1970 | 1000 | 50 |
| Pluronic ® 25R5 | 4500 | 2500 | 50 |
| Pluronic ® 10R8 | 5000 | 1000 | 80 |
| Pluronic ® 17R8 | 7500 | 1700 | 80 |
| Pluronic ® 25R8 | 9000 | 2500 | 80 |
| Tetronic ® 304 | 1650 | — | 40 |
| Tetronic ® 504 | 3400 | — | 40 |
| Tetronic ® 701 | 3600 | — | 10 |
| Tetronic ® 702 | 4000 | — | 20 |
| Tetronic ® 704 | 5500 | — | 40 |
| Tetronic ® 707 | 12000 | — | 70 |
| Tetronic ® 901 | 4700 | — | 10 |
| Tetronic ® 904 | 7500 | — | 40 |
| Tetronic ® 908 | 26100 | — | 80 |
| Tetronic ® 1101 | 5600 | — | 10 |
| Tetronic ® 1102 | 6300 | — | 20 |
| Tetronic ® 1104 | 8300 | — | 40 |
| Tetronic ® 1107 | 14500 | — | 70 |
| Tetronic ® 1301 | 6800 | — | 10 |
| Tetronic ® 1302 | 7800 | — | 20 |
| Tetronic ® 1304 | 10500 | — | 40 |
| Tetronic ® 1307 | 18600 | — | 70 |
| Tetronic ® 1501 | 7900 | — | 10 |
| Tetronic ® 1502 | 9000 | — | 20 |
| Tetronic ® 1504 | 12500 | — | 40 |
| Tetronic ® 1508 | 27000 | — | 80 |
| Tetronic ® 50R1 | 2640 | — | 10 |
| Tetronic ® 50R4 | 3740 | — | 40 |
| Tetronic ® 50R8 | 10200 | — | 80 |
| Tetronic ® 70R1 | 3400 | — | 10 |
| Tetronic ® 70R2 | 3870 | — | 20 |
| Tetronic ® 70R4 | 5230 | — | 40 |
| Tetronic ® 90R1 | 4580 | — | 10 |
| Tetronic ® 90R4 | 7240 | — | 40 |
| Tetronic ® 90R8 | 18700 | — | 80 |
| Tetronic ® 110R1 | 5220 | — | 10 |
| Tetronic ® 110R2 | 5900 | — | 20 |
| Tetronic ® 110R7 | 13200 | — | 70 |
| Tetronic ® 130R1 | 6800 | — | 10 |
| Tetronic ® 130R2 | 7740 | — | 20 |
| Tetronic ® 150R1 | 8000 | — | 10 |
| Tetronic ® 150R4 | 11810 | — | 40 |
| Tetronic ® 150R7 | 20400 | — | 70 |

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

Availability of Formulation Ingredients:
Pluronic® and Tetronic® surfactants—BASF Corporation
Triton™ surfactants—Dow Chemical Company
Citric acid (other acids or salts)—Sigma Aldrich
Hydrogen Peroxide solutions, 3% or 30%—Sigma Aldrich Peracetic acid—FMC Corporation or Sigma Aldrich
Peroxy compounds—Arkema Inc.

LIST OF RELEVANT PATENTS

| U.S. Pat. No. | Inventor |
|---|---|
| 3,912,451 | Gaglia |
| 3,982,892 | Gray |
| 4,051,058 | Bowing |
| 4,051,059 | Bowing |
| 4,431,631 | Clipper |
| 4,404,191 | Sporkenbach |
| 4,537,778 | Clipper |
| 4,536,314 | Hardy |
| 4,743,447 | Le Rouzic |
| 5,116,575 | Baderstscher |
| 5,171,564 | Nathoo |
| 5,296,239 | Colery |
| 5,489,706 | Revell |
| 5,605,687 | Lee |
| 5,589,106 | Shim |
| 5,900,256 | Scoville |
| 6,197,784 | Fuchs |
| 6,290,935 | Masters |
| 6,346,279 | Rochan |
| 6,585,933 | Ehrhardt |
| 6,656,426 | Wang |
| 6,683,040 | Bragulla |
| 6,686,325 | Ramarez |
| 6,693,069 | Korber |
| 6,696,093 | Ney |
| 6,716,457 | Eagles |
| 6,720,355 | Prusiner |
| 6,767,569 | Marsden |
| 6,790,380 | Sato |
| 6,797,681 | Fricker |
| 6,828,294 | Kellar |
| 6,908,891 | Biering |
| 6,936,434 | McDonnell |
| 6,998,369 | Hei |
| 7,001,873 | McDonnell |
| 7,008,592 | Sias |
| 7,049,277 | Bragulla |
| 7,074,374 | Fujii |
| 7,129,080 | Antloga |
| 5,840,343 | Hall, II |
| 5,656,302 | Cosentino |
| 5,616,616 | Hall, II |
| 5,508,646 | Cosentino |
| 5,344,652 | Hall, II |

What is claimed is:

1. An anti-microbial composition comprising:
a given amount of a given surfactant selected from the group consisting of 0.6%, 1%-4%, 6% and 10% of a poloxamer L-31, 0.6%, 3%, 4% and 6% of a poloxamer L-43, 3% of a poloxamer L-61, 2%, 3% and 4% of a poloxamer L-121, 0.1% of a poloxamer F-38, 6% of a poloxamer F-87, 2% of a poloxamer F-127 and 6% octylphenol ethoxylate 7.5, the poloxamer L-31 including an approximate molecular weight of propylene oxide/ethylene oxide block copolymer of 1100, an approximate molecular weight of the propylene oxide block of 950, and approximately 10% ethylene oxide content in the propylene oxide/ethylene oxide block copolymer, the poloxamer L-43 including an approximate molecular weight of propylene oxide/ethylene oxide block copolymer of 2500, an approximate molecular weight of the propylene oxide block of 1750, and approximately 20% ethylene oxide content in the propylene oxide/ethylene oxide block copolymer, the poloxamer L-61 including an approximate molecular weight of propylene oxide/ethylene oxide block copolymer of 2000, an approximate molecular weight of the propylene oxide block of 1750, and approximately 10% ethylene oxide content in the propylene oxide/ethylene oxide block copolymer, the poloxamer L-121 including an approximate molecular weight of propylene oxide/ethylene oxide block copolymer of 4400, an approximate molecular weight of the propylene oxide block of 4000, and approximately 10% ethylene oxide content in the propylene oxide/ethylene oxide block copolymer, the poloxamer F-38 including an approximate molecular weight of propylene oxide/ethylene oxide block copolymer of 5000, an approximate molecular weight of the propylene oxide block of 950, and approximately 80% ethylene oxide content in the propylene oxide/ethylene oxide block copolymer, the poloxamer F-87 including an approximate molecular weight of propylene oxide/ethylene oxide block copolymer of 7700, an approximate molecular weight of the propylene oxide block of 2250, and approximately 70% ethylene oxide content in the propylene oxide/ethylene oxide block copolymer, the poloxamer F-127 including an approximate molecular weight of propylene oxide/ethylene oxide block copolymer of 12500, an approximate molecular weight of the propylene oxide block of 4000, and approximately 70% ethylene oxide content in the propylene oxide/ethylene oxide block copolymer;
citric acid;
hydrogen peroxide; and
peracetic acid;
wherein the citric acid:hydrogen peroxide; peracetic acid ratio is equivalent to 0.7-3 citric acid:0.7-3 hydrogen peroxide:1-1.4 peracetic acid by weight; and
the composition is not corrosive to ferrous metal after at least 2 hours of contact with the metal.

2. The anti-microbial composition of claim 1 further comprising water.

3. The anti-microbial composition of claim 1 further comprising a lower alkyl alcohol wherein the alkyl group contains from 1 to 8 carbon atoms.

4. The anti-microbial composition of claim 3 wherein the alcohol is selected from the group consisting of methyl alcohol, ethyl alcohol, 1-propanol, 2-propanol, 1-butanol, 2-butanol, t-butanol, butyl cellusolve and combinations thereof.

5. The anti-microbial composition of claim 2 further comprising:
an organic salt.

6. The anti-microbial composition of claim 5 wherein the salt is selected from the group consisting of sodium citrate, potassium phthalate, sodium benzoate and combinations thereof.

7. The anti-microbial composition of claim 5 wherein the organic salt is a salt of citric acid.

8. The anti-microbial composition of claim 1 wherein the surfactant is present in a concentration of about 1% to 6% by weight, the citric acid is present in a concentration of about 0.01% to 20% by weight, the hydrogen peroxide is present in a concentration of about 0.1% to 20% by weight; and the peracetic acid is present in a concentration of about 0.05% to 30% by weight.

9. The anti-microbial composition of claim 1 wherein the surfactant is present in a concentration of about 3% to 4% by weight; the citric acid is present in a concentration of about 0.02% to 15% by weight, the hydrogen peroxide is present in a concentration of about 0.4% to 15% by weight, and the peracetic acid is present in a concentration of about 0.2% to 20% by weight.

10. The anti-microbial composition of claim 9 wherein the surfactant is present in a concentration of about 0.10% to 10% by weight; the citric acid is present in a concentration of about 0.6% to 10% by weight, the hydrogen peroxide is present in a concentration of about 0.7% to 10% by weight, and the peracetic acid is present in a concentration of about 0.3% to 14% by weight.

11. The anti-microbial composition of claim 1 which exhibits a zone of inhibition having a diameter of 25 mm to 70 mm; a Plate Cidality against each of *Staphylococcus aureus, Escherichia coli, Pseudomonas aeruginosa*, and *Candida albicans* at aqueous dilutions up to 1:2000; and is CPE positive.

12. The anti-microbial composition of claim 1 further
comprising an additional non-cationic antimicrobial agent which is different from the peroxy compound or peracetic acid.

13. The anti-microbial composition of claim 12 wherein the additional non-cationic antimicrobial agent is selected from the group consisting of phenolics, halogenated phenolics, halogenated diphenyl ethers, and halogenated carbonilides, peroxy oxidizing agents, and combinations thereof.

14. The anti-microbial composition of claim 1 further comprising: a wetting agent present an amount of from about 0.1 to 3% by weight.

15. The anti-microbial composition of claim 1 which exhibits an anti-microbial effect on microbes selected from the group consisting of *bacillus anthracis* and *clostridium difficile*.

16. The anti-microbial composition of claim 1 in the form of soap.

17. The antimicrobial composition of claim 1 which comprises about 0.1% poloxamer, about 1.8% citric acid, about 1.8% hydrogen peroxide, and about 0.6% peracetic acid, with the balance being water containing about 100 ppm sodium pyrophosphate.

18. The antimicrobial composition of claim 1 which comprises about 0.1% poloxamer, about 1.8% citric acid, about 1.8% hydrogen peroxide, about 0.6% peracetic acid, and about 3.0% t-butyl hydroperoxide, with the balance being water containing about 100 ppm sodium pyrophosphate.

19. The antimicrobial composition of claim 1 which comprises about 0.1% poloxamer, about 3.0% citric acid, about 3.0% hydrogen peroxide, about and 3.0% peracetic acid, with the balance being water containing about 100 ppm sodium pyrophosphate.

20. The antimicrobial composition of claim 1 which comprises about 0.1% poloxamer, about 1.8% sodium citrate, about 1.8% hydrogen peroxide, 0.6% peracetic acid, about and 4.0% ethanol, with the balance being water containing about 100 ppm sodium pyrophosphate.

* * * * *